US009347054B2

(12) United States Patent
Bossard et al.

(10) Patent No.: US 9,347,054 B2
(45) **Date of Patent: *May 24, 2016**

(54) POLYMER FACTOR IX MOIETY CONJUGATES

(71) Applicant: NEKTAR THERAPEUTICS, San Francisco, CA (US)

(72) Inventors: Mary J. Bossard, Madison, AL (US); Gayle Stephenson Phillips, Harvest, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/076,116

(22) Filed: Nov. 8, 2013

(65) Prior Publication Data

US 2014/0141483 A1 May 22, 2014

Related U.S. Application Data

(63) Continuation of application No. 12/638,811, filed on Dec. 15, 2009, now Pat. No. 8,586,711, which is a continuation of application No. 12/499,770, filed on Jul. 8, 2009, now abandoned, which is a continuation of application No. 11/172,459, filed on Jun. 30, 2005, now Pat. No. 7,579,444.

(60) Provisional application No. 60/584,505, filed on Jun. 30, 2004.

(51) Int. Cl.

| | |
|---|---|
| *C07K 14/745* | (2006.01) |
| *C12N 9/96* | (2006.01) |
| *A61K 47/48* | (2006.01) |
| *C12N 9/64* | (2006.01) |

(52) U.S. Cl.

CPC ........... *C12N 9/96* (2013.01); *A61K 47/48215* (2013.01); *C12N 9/644* (2013.01)

(58) Field of Classification Search

CPC .................................................... C07K 14/745
USPC ......................................... 530/384, 402, 324
See application file for complete search history.

(56) References Cited

U.S. PATENT DOCUMENTS

| | | | |
|---|---|---|---|
| 4,179,337 | A | 12/1979 | Davis et al. |
| 4,361,510 | A | 11/1982 | Mitra |
| 4,470,968 | A | 9/1984 | Mitra et al. |
| 4,770,999 | A | 9/1988 | Kaufman et al. |
| 4,786,726 | A | 11/1988 | Smith |
| 5,171,569 | A | 12/1992 | Anson et al. |
| 5,409,990 | A | 4/1995 | Linnau et al. |
| 5,460,950 | A | 10/1995 | Barr et al. |
| 5,559,213 | A | 9/1996 | Hakimi et al. |
| 5,614,500 | A | 3/1997 | Zimmermann |
| 5,621,039 | A | 4/1997 | Hallahan et al. |
| 5,629,384 | A | 5/1997 | Veronese et al. |
| 5,637,749 | A | 6/1997 | Greenwald |
| 5,714,583 | A | 2/1998 | Foster et al. |
| 5,770,700 | A | 6/1998 | Webb et al. |
| 5,925,738 | A | 7/1999 | Miekka et al. |
| 5,965,425 | A | 10/1999 | Barr et al. |
| 5,969,040 | A | 10/1999 | Hallahan et al. |
| 6,037,452 | A | 3/2000 | Minamino et al. |
| 6,048,720 | A | 4/2000 | Dalborg et al. |
| 6,159,722 | A | 12/2000 | Bode et al. |
| 6,320,029 | B1 | 11/2001 | Miekka et al. |
| 6,372,716 | B1 | 4/2002 | Bush et al. |
| 6,423,826 | B1 | 7/2002 | Nelsestuen |
| 6,566,506 | B2 | 5/2003 | Greenwald et al. |
| 6,660,843 | B1 | 12/2003 | Feige et al. |
| 6,710,031 | B2 | 3/2004 | Fukuchi et al. |
| 6,753,165 | B1 | 6/2004 | Cox et al. |
| 6,835,809 | B1 | 12/2004 | Liu et al. |
| 7,125,843 | B2 | 10/2006 | DeFrees et al. |
| 7,329,516 | B2 | 2/2008 | Li et al. |
| 7,579,444 | B2 | 8/2009 | Bossard et al. |
| 2003/0143596 | A1 | 7/2003 | Bentley et al. |
| 2004/0106779 | A1 | 6/2004 | Bigler et al. |
| 2004/0137557 | A1 | 7/2004 | Defrees et al. |
| 2004/0167287 | A1 | 8/2004 | Kozlowski et al. |
| 2004/0180054 | A1 | 9/2004 | Kim et al. |
| 2005/0026834 | A1 | 2/2005 | Cox, III et al. |
| 2005/0063943 | A1 | 3/2005 | Sommermeyer et al. |
| 2005/0100982 | A1 | 5/2005 | DeFrees et al. |
| 2005/0114037 | A1 | 5/2005 | Desjarlais et al. |
| 2005/0176108 | A1 | 8/2005 | Kim et al. |

(Continued)

FOREIGN PATENT DOCUMENTS

| | | | |
|---|---|---|---|
| AU | 2004/096860 | A1 | 12/2004 |
| EP | 1260582 | A1 | 11/2002 |

(Continued)

OTHER PUBLICATIONS

Caliceti et al., "Pharmacokinetic and biodistribution properties of poly(ethylene glycol)-protein conjugates", Adv. Drug Del. Rev., vol. 55, pp. 1261-1277, (2003).

(Continued)

*Primary Examiner* — David Lukton

(74) *Attorney, Agent, or Firm* — Susan T. Evans; Mark A. Wilson; McDermott Will & Emery LLP

(57) ABSTRACT

Conjugates of a Factor IX moiety and one or more water-soluble polymers are provided. Typically, the water-soluble polymer is polyethylene glycol) or a derivative thereof. Also provided (among other things) are compositions comprising the conjugates, methods of making the conjugates, and methods of administering to a patient compositions comprising the conjugates.

14 Claims, 7 Drawing Sheets

(56) References Cited

U.S. PATENT DOCUMENTS

| | | | |
|---|---|---|---|
| 2005/0221431 | A1 | 10/2005 | Backer et al. |
| 2006/0052302 | A1 | 3/2006 | Bossard et al. |
| 2006/0115876 | A1 | 6/2006 | Pan et al. |

FOREIGN PATENT DOCUMENTS

| | | | |
|---|---|---|---|
| WO | WO 90/12874 | A2 | 11/1990 |
| WO | WO 94/04193 | | 3/1994 |
| WO | WO 94/18247 | | 8/1994 |
| WO | WO 94/29370 | A1 | 12/1994 |
| WO | WO 97/11957 | | 4/1997 |
| WO | WO 03/031464 | A2 | 4/2003 |
| WO | WO 03/040211 | | 5/2003 |
| WO | WO 2004/033651 | A2 | 4/2004 |
| WO | WO 2006/005058 | | 1/2006 |

OTHER PUBLICATIONS

Veronese, "Peptide and protein PEGylation: a review of problems and solutions", Biomaterials, vol. 22, pp. 405-417, (2001).

Enzon Pharmaceuticals, Macromolecular Engineering Technologies, pp. 1-14, (2004).

NEKTAR™—Transforming Therapeutics, Nektar Molecule Engineering: Polyethylene Glycol and Derivatives for Advanced PEGylation, pp. 1-20, (Catalog—2003).

NEKTAR™—Transforming Therapeutics, Nektar Advanced PEGylation: Polyethylene Glycol and Derivatives for Advanced PEGylation, pp. 1-24, (Catalog—2004).

NOF Corporation, "PEG Derivatives, Phospholipid and Drug Delivery Materials for Pharmaceuticals", pp. 1-46, (Catalogue 2003-1st).

NOF Corporation, "PEG Derivatives, Phospholipid and Drug Delivery Materials for Pharmaceuticals", pp. 1-50, (Catalogue 2003-2nd).

Polypure, Products; PEG amines; PEG acids and amino acids; PEG thiols and disulfides; Biotins, (Apr. 2004).

Polypure, Products; PEG amines; PEG acids and amino acids; PEG thiols and disulfides; Biotins, (Apr. 2005).

Quanta BioDesign, Labeling, Derivatization and Crosslinking Reagents for Biological and Related Materials with dPEG™, pp. 1-38, (Mar. 12, 2004).

Quanta BioDesign, Labeling, Modification and Crosslin king Reagents monodispersed dPEG™ Technology, pp. 1-31, (Nov. 5 2004).

Shearwater Polymers, Inc., p. 2-49, (Catalog—Mar. 1995).

Shearwater Polymers, Inc., Polyethylene Glycol and Derivatives, pp. 1-53, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—2000).

Shearwater Corporation, Polyethylene Glycol and Derivatives for Biomedical Applications, pp. 1-17, (Cataloag—2001).

European Patent Office Communication dated Jan. 22, 2008 in European Patent Application No. 05787845.0.

Written Opinion of the ISA in PCT Application No. PCT/US2005/023745 mail date Jan. 18, 2007.

Benhar et al , "Pseudomonas Exotoxin A Mutants", J. Biol. Chem., vol. 269. No. 18. pp. 13398-13404 (1994).

Tsutsumi et al., "Site-specific chemical modification with polyethelene glycol of recombinant immunotoxin anti-Tac(Fv)-PE38 (LMB-2) improves antitumor activity and reduces animal toxicity and immunogenicity", PNAS USA, vol. 97, No. 15, pp. 8548-8553 (2000).

Yang et al., "Tailoring structure-funtion and pharmacokinetic properties of single-chain Fv proteins by site-specific PEGylation", Protein Engineering, vol. 16, No. 10, pp. 761-770 (2003).

POLYMER FACTOR IX MOIETY CONJUGATES

CROSS REFERENCE TO RELATED APPLICATIONS

This application is a continuation of U.S. patent application Ser. No. 12/638,811, filed Dec. 15, 2009, now U.S. Pat. No. 8,586,711, which is a continuation of U.S. patent application Ser. No. 12/499,770, filed Jul. 8, 2009, now abandoned, which is a continuation of U.S. patent application Ser. No. 11/172,459, now U.S. Pat. No. 7,579,444, filed Jun. 30, 2005, which claims the benefit of priority to U.S. Provisional Patent Application No. 60/584,505, filed Jun. 30, 2004, all of which are incorporated herein by reference.

FIELD OF THE INVENTION

The present invention relates generally to conjugates comprising a Factor IX moiety (i.e., a moiety having Factor IX activity) and a polymer. In addition, the invention relates to compositions comprising the conjugates, methods for synthesizing the conjugates, methods for delivering the conjugates, and methods for treating patients.

REFERENCE TO SEQUENCE LISTING, TABLE OR COMPUTER PROGRAM

A Sequence Listing is being submitted electronically via EFS in the form of a text file, created Nov. 1, 2013 and named "0915340405seqlist.txt" (4,423 bytes), the contents of which are incorporated herein by reference in their entirety.

BACKGROUND OF THE INVENTION

Hemostasis is the process of arresting the outflow of blood from an injured blood vessel. For mammals, as well as many other organisms, the hemostatic process is critically important for continued survival. Defects in the hemostatic process can result in, for example, the inability to effectively form blood clots that serve to stop the loss of blood following vascular injury. In humans, individuals who suffer from an inability to form blood clots are called hemophiliacs. Of particular concern for hemophiliacs is the life-threatening risk that once started, bleeding will never cease.

Generally, hemophiliacs lack the ability to produce effective amounts of one or more substances ultimately required for the transformation of soluble fibrinogen into insoluble fibrin. For example, hemophiliacs who suffer from hemophilia B (also called "congenital factor IX deficiency" and "Christmas disease") have an inability to produce effective levels of Factor IX. Factor IX is a key component of one of several "cascades" of reactions that result in the formation of blood clots. Critical for the cascade of reactions referred to as the "intrinsic pathway," Factor IX ultimately influences the conversion of fibrinogen into the major component of blood clots, fibrin.

Although the process by which blood clots are formed is relatively complex, the role of Factor IX in the intrinsic pathway can be described briefly. When blood comes into contact with negatively charged surfaces and/or subendothelial connective tissues (as a result of, for example, tissue damage associated with a laceration), Factor XII (or Hageman factor) in the presence of other substances is transformed into Factor XIIa. Factor XIIa (along with other substances) transforms Factor XI into Factor XIa. In turn, Factor XIa (along with other substances) transforms Factor IX into Factor IXa. Factor VIII, Factor IXa, calcium ions and phospholipid micelles form a lipoprotein complex with Factor X and activate it to form Factor Xa. Thereafter, Factor Xa (along with other substances) converts prothrombin into thrombin, with the result that a relatively large amount of thrombin is produced over time. Relatively large amounts of thrombin convert fibrinogen into fibrin. Fibrin, in turn, forms the matrix or lattice responsible for the formation of blood clots. Factor IX's role in the intrinsic pathway of blood clotting is shown schematically in FIG. 13.

Affecting one out of 34,500 males, hemophilia B can result from any one of a variety of mutations of the Factor IX gene, which is located on the X-chromosome. Depending on the particular mutation, hemophilia B can manifest itself as severe, moderate or mild. Individuals suffering from the severest forms of hemophilia B entirely lack the ability to express active forms of Factor IX. Clinically, individuals affected with hemophilia B suffer from nose bleeds, easy bruising, joint hemorrhage, and prolonged bleeding from wounds. Current treatment of hemophilia B involves the infusion of exogenous Factor IX concentrate collected from human plasma or prepared via recombinant DNA techniques. Because these treatments serve only to supplement the lack of effective levels of Factor IX, individuals suffering from severe forms of hemophilia B require regular injections (as often as three times a week) of Factor IX concentrate throughout their lives. Patients suffering from even more moderate forms of hemophilia B often require injection of Factor IX concentrate before and/or following surgery and dental work.

Several commercial forms of Factor IX concentrates are available to provide replacement therapy for patients suffering from hemophilia B. For example, blood-derived Factor IX complex products (containing other factors) are sold under the BEBULIN VH® (Baxter Healthcare, Vienna, Austria), KONYNE 80® (Bayer Corporation, Eikhart Ind.), PROFILNINE SD™ (Alpha Therapeutic Corporation, Los Angeles Calif.), and PROPLEX T® (Baxter Healthcare, Glendale Calif.) brands. Somewhat more purified forms of Factor IX products are sold under the ALPHANINE SD® (Alpha Therapeutic Corporation, Los Angeles Calif.) and MONONINE® (Aventis Behring, Kankakee Ill.) brands. With respect to recombinantly prepared Factor IX concentrates, one product is currently available under the BENEFIX® (Wyeth/Genetics Institute, Cambridge Mass.) brand.

Generally, the recombinant source of Factor IX concentrate is favored over blood-derived sources since the latter involves the risk of transmitting viruses and/or other diseases. In addition, purity is often higher with the recombinant source, thereby avoiding potential problems arising from administering unwanted blood factors and other proteins generally present in blood-derived sources.

Notwithstanding the benefits of administering a recombinant-based formulation, the processing of recombinant-based products often requires the presence of certain proteins such as albumin, which can be present in the final formulation administered to the patient. As a result, patients who receive such formulations develop allergic reactions to these foreign proteins. In any event, both blood-derived and recombinant-based products suffer from the disadvantage of repeated administration.

PEGylation, or the attachment of a poly(ethylene glycol) derivative to a protein, has been described as a means to reduce immunogenicity as well as a means to prolong a protein's in vivo half-life. With respect to Factor IX, however, previous approaches for forming protein-polymer conjugates suffered from several deficiencies.

For example, U.S. Pat. No. 5,969,040 describes a process comprising the step of oxidizing vicinal dials of carbohydrate moieties in the activation region of Factor IX to form aldehydes. Following the oxidizing step, the described process includes the step of covalently attaching one or more non-antigenic polymers [such as a hydrazine-bearing poly(ethylene glycol) derivative] to the oxidized carbohydrate moieties. A problem with this approach, however, is the increased complexity attributed to the additional steps required to obtain an oxidized form of Factor IX. In addition, any oxidizers that may remain following the oxidation step may degrade the polymer associated with the conjugate. Finally, this approach is limited to conjugation using specific polymers (i.e., hydrazide-containing polymers) and specific regions on Factor IX (i.e., vicinal diols of carbohydrate moieties in the activation region of Factor IX).

The presence of oxidizers (present either as a result of the process described in U.S. Pat. No. 5,969,040, or from other causes) introduces additional challenges with respect to providing an acceptable pharmaceutical product of a polymer conjugated to Factor IX. Specifically, methionine and other hydroxyl-containing amino acids may be subject to unwanted oxidation in the presence of oxidizers, thereby introducing aldehyde groups. Any residual aldehydes not reacted with the polymeric reagent will be reactive and can potentially damage the protein. In order to address this problem, unreacted aldehydes need to be capped with glycine or other small molecule to stabilize the protein. In doing so, however, an analytical problem arises in that for regulatory purposes, a product should be readily defined; the introduction of additional components can frustrate otherwise straightforward product definition. In particular, the use of capping agents would present a particularly difficult challenge.

U.S. Pat. No. 6,037,452 describes attachment of a poly (alkylene oxide) to Factor IX, wherein attachment to Factor IX is effected through a poly(alkylene oxide) bearing one of the following reactive groups: triazine, acetyl, hydrazine, diazonium, amino, and succinimidyl ester. Again, however, the reference lacks disclosure of effecting attachment through polymers bearing reactive groups other than triazine, acetyl, hydrazine, diazonium, amino, or succinimidyl ester.

Thus, there remains a need in the art to provide additional conjugates between water-soluble polymers and moieties having Factor IX activity. In particular, there is a need to provide more simple processes for conjugating a polymer to a moiety having Factor IX activity. The present invention is therefore directed to such conjugates as well as compositions comprising the conjugates and related methods as described herein, which are believed to be new and completely unsuggested by the art.

SUMMARY OF THE INVENTION

Accordingly, in one or more embodiments of the invention, a conjugate is provided, the conjugate comprising a Factor IX moiety covalently attached, either directly or through a spacer moiety comprised of one or more atoms, to a water-soluble polymer, wherein the molecular weight of the water-soluble polymer is greater than 5,000 Daltons and less than about 150,000 Daltons.

In one or more embodiments of the invention, a conjugate is provided, the conjugate comprising a Factor IX moiety covalently attached at an amino acid residue, either directly or through a spacer moiety comprised of one or more atoms, to a water-soluble polymer, wherein the amino acid residue is not attached, either directly or through the spacer moiety, via a $—CH_2—C(O)—O—$, $—N(H)—C(O)CH_2—O—$, $—C(O)—N(H)—$, $—N(H)—C(O)—CH_2—O—$, $—C(O)—CH_2—O—$, $—C(O)—CH_2—CH_2—C(O)—O—$, diazo, or triazine linkage.

In one or more embodiments of the invention, a conjugate is provided, the conjugate comprising a Factor IX moiety covalently attached, either directly or through a spacer moiety comprising of one or more atoms to a non-linear water-soluble polymer.

In one or more embodiments of the invention, a composition is provided, the composition comprising a plurality of conjugates, wherein at least about 80% of all conjugates in the composition are each comprised of a Factor IX moiety covalently attached to one, two, three or four water-soluble polymers, and further wherein for each water-soluble polymer in the conjugate, the Factor IX moiety is attached either directly or through a spacer moiety comprised of one or more atoms. The compositions encompass all types of formulations and in particular those that are suited for injection such as powders that can be reconstituted, as well as liquids (e.g., suspensions and solutions).

In one or more embodiments of the invention, a method for preparing a conjugate is provided, the method comprising adding a polymeric reagent composition to a Factor IX composition under conditions sufficient to result in a conjugate comprising a Factor IX moiety covalently attached, either directly or through a spacer moiety comprised of one or more atoms, to a water-soluble polymer.

In one or more embodiments of the invention, a method for delivering a conjugate is provided, the method comprising administering to the patient a composition comprising a conjugate as described herein. The step of administering the conjugate can be effected by injection (e.g., intramuscular injection, intravenous injection, subcutaneous injection, and so forth) or other approach.

DETAILED DESCRIPTION OF THE INVENTION

Figure 1:
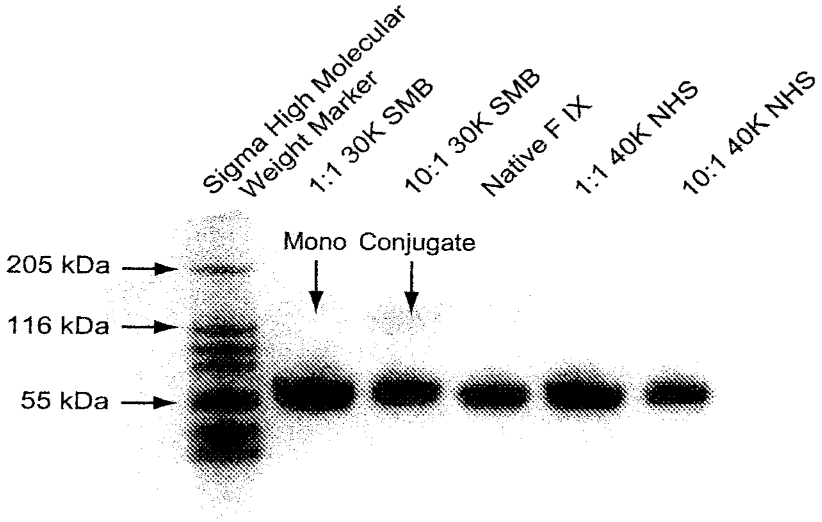
FIG. 1 and FIG. 2 are copies of gels resulting from sodium dodecyl sulfate-polyacrylamide gel electrophoresis (SDS-PAGE) analysis of samples described in Examples 1 through 4.

Before describing one or more embodiments of the present invention in detail, it is to be understood that this invention is not limited to the particular polymers, synthetic techniques, Factor IX moieties, and the like, as such may vary.

It must be noted that, as used in this specification and the claims, the singular forms "a," "an," and "the" include plural referents unless the context clearly dictates otherwise. Thus, for example, reference to "a polymer" includes a single polymer as well as two or more of the same or different polymers, reference to "an optional excipient" refers to a single optional excipient as well as two or more of the same or different optional excipients, and the like.

In describing and claiming the present invention, the following terminology will be used in accordance with the definitions described below.

"PEG," "polyethylene glycol" and "poly(ethylene glycol)" as used herein, are interchangeable. Typically, PEGs for use in accordance with the invention comprise the following structure "$—(OCH_2CH_2)_n—$" where (n) is 2 to 4000. As used herein, PEG also includes "$—CH_2CH_2—O(CH_2CH_2O)_n—CH_2CH_2—$" and "$—(OCH_2CH_2)_nO—$," depending upon whether or not the terminal oxygens have been displaced. Throughout the specification and claims, it should be remembered that the term "PEG" includes structures having various terminal or "end capping" groups and so forth. The term "PEG" also means a polymer that contains a majority, that is to say, greater than 50%, of $—OCH_2CH_2—$ repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3O(CH_2CH_2O)_n—$] or not [e.g., "$CH_3$" in $CH_3(OCH_2CH_2)_n—$] In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and any resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer as described herein, means a polymer that in its entirety is not found in nature. A non-naturally occurring polymer may, however, contain one or more monomers or segments of monomers that are naturally occurring, so long as the overall polymer structure is not found in nature.

The term "water soluble" as in a "water-soluble polymer" is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a water-soluble polymer, such as PEG, can be expressed as either a number-average molecular weight or a weight-average molecular weight. Unless otherwise indicated, all references to molecular weight herein refer to the weight-average molecular weight. Both molecular weight determinations, number-average and weight-average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03. As used herein, references will at times be made to a single water-soluble polymer having either a weight-average molecular weight or number-average molecular weight; such references will be understood to mean that the single-water soluble polymer was obtained from a composition of water-soluble polymers having the stated molecular weight.

The terms "active" or "activated" when used in conjunction with a particular functional group, refer to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" and "linker" are used herein to refer to an atom or a collection of atoms optionally used to link interconnecting moieties such as a terminus of a water-soluble polymer and a Factor IX moiety or an electrophile or nucleophile of a Factor IX moiety. The spacer moiety may be hydrolytically stable or may include a physiologically hydrolyzable or enzymatically degradable linkage.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically non-reactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl and substituted aryl.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or with an electrophile.

A "physiologically cleavable" or "hydrolyzable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient" refers to an excipient that may optionally be included in the compositions of the invention and that causes no significant adverse toxicological effects to the patient.

"Therapeutically effective amount" is used herein to mean the amount of a polymer-Factor IX moiety conjugate that is needed to provide a desired level of the conjugate (or corresponding unconjugated Factor IX moiety) in the bloodstream or in the target tissue. The precise amount will depend upon numerous factors, e.g., the particular Factor IX moiety, the components and physical characteristics of the therapeutic composition, intended patient population, mode of delivery, individual patient considerations, and the like, and can readily be determined by one skilled in the art, based upon the information provided herein.

"Multi-functional" means a polymer having three or more functional groups contained therein, where the functional groups may be the same or different. Multi-functional polymeric reagents will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

The term "Factor IX moiety," as used herein, refers to a moiety having Factor IX activity. The Factor IX moiety will also have at least one electrophilic group or nucleophilic group suited for reaction with a polymeric reagent. Typically, although not necessarily, the Factor IX moiety is a protein. In addition, the term "Factor IX moiety" encompasses both the Factor IX moiety prior to conjugation as well as the Factor IX moiety residue following conjugation. As will be explained in further detail below, one of ordinary skill in the art can determine whether any given moiety has Factor IX activity. A protein comprising an amino acid sequence corresponding to SEQ ID NO: 1 is a Factor IX moiety, as well as any protein or polypeptide substantially homologous thereto, whose biological properties result in the activity of Factor IX. As used herein, the term "Factor IX moiety" includes proteins modified deliberately, as for example, by site directed mutagenesis or accidentally through mutations. The term "Factor IX moiety" also includes derivatives having from 1 to 6 additional glycosylation sites, derivatives having at least one additional amino acid at the carboxy terminal end of the protein wherein the additional amino acid(s) includes at least one glycosylation site, and derivatives having an amino acid sequence which includes at least one glycosylation site.

The term "substantially homologous" means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, sequences having greater than 95 percent homology, equivalent biological properties (although potentiality different degrees of activity), and equivalent expression characteristics are considered substantially homologous. For purposes of determining homology, truncation of the mature sequence should be disregarded. Sequences having lesser degrees of homology, comparable bioactivity, and equivalent expression characteristics are considered substantial equivalents. Exemplary Factor IX moieties for use herein include those proteins having a sequence that is substantially homologous to SEQ ID NO: 1.

The term "fragment" means any protein or polypeptide having the amino acid sequence of a portion of a Factor IX moiety that retains some degree of Factor IX activity. Fragments include proteins or polypeptides produced by proteolytic degradation of the Factor IX protein or produced by chemical synthesis by methods routine in the art. Determining whether a particular fragment has the biological activity of Factor IX can carried out by conventional, well known tests utilized for such purposes on one or more species of mammals. An appropriate test which can be utilized to demonstrate such biological activity is described herein.

A "deletion variant" of a Factor IX moiety is peptide or protein in which one amino acid residue of the Factor IX moiety has been deleted and the amino acid residues preceding and following the deleted amino acid residue are connected via an amide bond (except in instances where the deleted amino acid residue was located on a terminus of the peptide or protein). Deletion variants include instances where only a single amino acid residue has been deleted, as well as instances where two amino acids are deleted, three amino acids are deleted, four amino acids are deleted, and so forth. Each deletion variant must, however, retain some degree of Factor IX activity.

A "substitution variant" of a Factor IX moiety is peptide or protein in which one amino acid residue of the Factor IX moiety has been deleted and a different amino acid residue has taken its place. Substitution variants include instances where only a single amino acid residue has been substituted, as well as instances where two amino acids are substituted, three amino acids are substituted, four amino acids are substituted, and so forth. Each substitution variant must, however, have some degree of Factor IX activity.

An "addition variant" of a Factor IX moiety is peptide or protein in which one amino acid residue of the Factor IX moiety has been added into an amino acid sequence and adjacent amino acid residues are attached to the added amino acid residue by way of amide bonds (except in instances where the added amino acid residue is located on a terminus of the peptide or protein, wherein only a single amide bond attaches the added amino acid residue). Addition variants include instances where only a single amino acid residue has been added, as well as instances where two amino acids are added, three amino acids are added, four amino acids are added, and so forth. Each addition variant must, however, have some degree of Factor IX activity.

The term "patient," refers to a living organism suffering from or prone to a condition that can be prevented or treated by administration of an active agent (e.g., conjugate), and includes both humans and animals.

"Optional" or "optionally" means that the subsequently described circumstance may or may not occur, so that the description includes instances where the circumstance occurs and instances where it does not.

"Substantially" (unless specifically defined for a particular context elsewhere or the context clearly dictates otherwise) means nearly totally or completely, for instance, satisfying one or more of the following: greater than 50%, 51% or greater, 75% or greater, 80% or greater, 90% or greater, and 95% or greater of the condition.

Unless the context clearly dictates otherwise, when the term "about" precedes a numerical value, the numerical value is understood to mean±10% of the stated numerical value.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is H is or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

Turning to one or more embodiments of the invention, a conjugate is provided, the conjugate comprising a Factor IX moiety covalently attached, either directly or through a spacer moiety comprised of one or more atoms, to a water-soluble polymer. The conjugates of the invention will have one or more of the following features.

The Factor IX Moiety

As previously stated, the term "Factor IX moiety" shall include the Factor IX moiety prior to conjugation as well as to the Factor IX moiety following attachment to a water-soluble polymer. It is understood, however, that when the Factor IX moiety is attached to a nonpeptidic water-soluble polymer, the Factor IX moiety is slightly altered due to the presence of one or more covalent bonds associated with linkage to the polymer (or spacer moiety that is attached to the polymer). Often, this slightly altered form of the Factor IX moiety attached to another molecule is referred to a "residue" of the Factor IX moiety.

The Factor IX moiety can be derived from either non-recombinant methods or from recombinant methods and the invention is not limited in this regard. In addition, the Factor IX moiety can be derived from human sources or from animal sources.

The Factor IX moiety can be derived non-recombinantly. For example, the Factor IX moiety can be obtained from blood-derived sources. In particular, Factor IX can be fractionated from human plasma using precipitation and centrifugation techniques known to those of ordinary skill in the art. See, for example, Wickerhauser (1976) *Transfusion* 16(4): 345-350 and Slichter et al. (1976) *Transfusion* 16(6):616-626. Factor IX can also be isolated from human granulocytes. See Szmitkoski et al. (1977) *Haematologia* (*Budap.*) 11(1-2):177-187.

The Factor IX moiety can be derived from recombinant methods. For example, the cDNA coding for native Factor IX, which is a Factor IX moiety, has been isolated, characterized, and cloned into expression vectors. See, e.g., Choo et al. (1982) "Molecular Cloning of the Gene for Human Anti-hemophilic Factor IX," Nature, Vol. 299: 178-180, and Kurachi et al. (1982) "Isolation and Characterization of a cDNA Coding for Human Factor IX," Proc. Natl. Acad. Sci. U.S.A., Vol. 79: 6461-65.

Once expressed, native Factor IX is a single chain glycoprotein of about 55,000 Daltons. It can structurally be considered as having four domains: the Gla or gamma carboxyglutamate-rich domain; the EGF-like regions; the activation peptide; and the active site. The expressed amino acid sequence is provided as SEQ ID NO: 1. Unless specifically noted, all assignments of a numeric location of an amino acid residue as provided herein are based on SEQ ID NO: 1.

Exemplary recombinant methods used to prepare a Factor IX moiety (whether native Factor IX or a different protein having Factor IX activity) can be briefly described. Such methods involve constructing the nucleic acid encoding the desired polypeptide or fragment, cloning the nucleic acid into an expression vector, transforming a host cell (e.g., plant, bacteria such as *E. coli*, yeast such as *Saccharomyces cerevisiae*, or mammalian cell such as Chinese hamster ovary cell or baby hamster kidney cell), and expressing the nucleic acid to produce the desired polypeptide or fragment. The expression can occur via exogenous expression (when the host cell naturally contains the desired genetic coding) or via endogenous expression. Methods for producing and expressing recombinant polypeptides in vitro and in prokaryotic and eukaryotic host cells are known to those of ordinary skill in the art. See, for example, U.S. Pat. No. 4,868,122.

To facilitate identification and purification of the recombinant polypeptide, nucleic acid sequences that encode for an epitope tag or other affinity binding sequence can be inserted or added in-frame with the coding sequence, thereby producing a fusion protein comprised of the desired polypeptide and a polypeptide suited for binding. Fusion proteins can be identified and purified by first running a mixture containing the fusion protein through an affinity column bearing binding moieties (e.g., antibodies) directed against the epitope tag or other binding sequence in the fusion proteins, thereby binding the fusion protein within the column. Thereafter, the fusion protein can be recovered by washing the column with the appropriate solution (e.g., acid) to release the bound fusion protein. The recombinant polypeptide can also be identified and purified by lysing the host cells, separating the polypeptide, e.g., by size exclusion chromatography, and collecting the polypeptide. These and other methods for identifying and purifying recombinant polypeptides are known to those of ordinary skill in the art. In one or more embodiments of the present invention, however, it is preferred that the Factor IX moiety is not in the form of a fusion protein.

Depending on the system used to express proteins having Factor IX activity, the Factor IX moiety can be unglycosylated or glycosylated and either may be used. That is, the Factor IX moiety can be unglycosylated or the Factor IX moiety can be glycosylated. In one or more embodiments of the invention, it is preferred that the Factor IX moiety is glycosylated.

The moiety having Factor IX activity can advantageously be modified to include one or more amino acid residues such as, for example, lysine, cysteine and/or arginine, in order to provide facile attachment of a polymer to an atom within an amino acid. In addition, the Factor IX moiety can be modified to include a non-naturally occurring amino acid residue. Techniques for adding amino acid residues and non-naturally occurring amino acid residues are well known to those of ordinary skill in the art. Reference is made to J. March, Advanced Organic Chemistry: Reactions Mechanisms and Structure, 4th Ed. (New York: Wiley-Interscience, 1992).

In addition, the Factor IX moiety can advantageously be modified to include attachment of a functional group (other than through addition of a functional group-containing amino acid residue). For example, the Factor IX moiety can be modified to include a thiol group. In addition, the Factor IX moiety can be modified to include an N-terminal alpha carbon. In addition, the Factor IX moiety can be modified to include one or more carbohydrate moieties. Factor IX moieties modified to contain an aminoxy, aldehyde or other functional group can also be used.

Nonlimiting examples of Factor IX moieties include the following: Factor IX; Factor IXa; truncated versions of Factor IX; hybrid proteins, and peptide mimetics having Factor IX activity. Biologically active fragments, deletion variants, substitution variants or addition variants of any of the foregoing that maintain at least some degree of Factor IX activity can also serve as a Factor IX moiety.

For any given moiety, it is possible to determine whether that moiety has Factor IX activity. For example, several animal lines have been intentionally bred with the genetic mutation for hemophilia such that an animal produced from such a line has very low and insufficient levels of Factor IX. Such lines are available from a variety of sources such as, without limitation, the Division of Laboratories and Research, New York Department of Public Health, Albany, N.Y. and the Department of Pathology, University of North Carolina, Chapel Hill, N.C. Both of these sources, for example, provide canines suffering from canine hemophilia B. In order to test the Factor IX activity of any given moiety in question, the moiety is injected into the diseased animal, a small cut made and bleeding time compared to a healthy control. Another method useful for determining Factor IX activity is to determine cofactor and procoagulant activity. See, for example, Mertens et al. (1993) *Brit. J. Haematol.* 85:133-42, Other methods known to those of ordinary skill in the art can also be used to determine whether a given moiety has Factor IX activity. Such methods are useful for determining the Factor IX activity of both a proposed Factor IX moiety as well as the corresponding polymer-Factor IX moiety conjugate.

The Water-Soluble Polymer

As previously discussed, each conjugate comprises a Factor IX moiety attached to a water-soluble polymer. With respect to the water-soluble polymer, the water-soluble polymer is nonpeptidic, nontoxic, non-naturally occurring and biocompatible. With respect to biocompatibility, a substance is considered biocompatible if the beneficial effects associated with use of the substance alone or with another substance (e.g., an active agent such a Factor IX moiety) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water-soluble polymer is biocompatible and nonimmunogenic.

Further the polymer is typically characterized as having from 2 to about 300 termini, Examples of such polymers include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), and combinations of any of the foregoing.

The polymer is not limited in a particular structure and can be linear (e.g., alkoxy PEG or bifunctional PEG), or nonlinear such as branched, forked, multi-armed (e.g., PEGs attached to a polyol core), and dendritic. Moreover, the internal structure of the polymer can be organized in any number of different patterns and can be selected from the group consisting of homopolymer, alternating copolymer, random copolymer, block copolymer, alternating tripolymer, random tripolymer, and block tripolymer.

Typically, activated PEG and other activated water-soluble polymers (i.e., polymeric reagents) are activated with a suitable activating group appropriate for coupling to a desired site on the Factor IX moiety. Thus, a polymeric reagent will possess a reactive group for reaction with the Factor IX moiety. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), and in Zalipsky (1995) *Advanced Drug Reviews* 16: 157-182.

Typically, the weight-average molecular weight of the water-soluble polymer in the conjugate is from about 100 Daltons to about 150,000 Daltons. Exemplary ranges, however, include weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight-average molecular weight of less than about 6,000 Daltons.

When used as the polymer, PEGs will typically comprise a number of ($OCH_2CH_2$) monomers [or ($CH_2CH_2O$) monomers, depending on how the PEG is defined]. As used throughout the description, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

With regard to the molecular weight of the water-soluble polymer, in or more embodiments of the invention, a conjugate is provided, the conjugate comprising a Factor IX moiety covalently attached, either directly or through a spacer moiety comprised of one or more atoms, to a water-soluble polymer, wherein the molecular weight of the water-soluble polymer is greater than 5,000 Daltons and less than about 150,000 Daltons.

One particularly preferred polymer for use in the invention is an end-capped polymer, that is, a polymer having at least one terminus capped with a relatively inert group, such as a lower $C_{1-6}$ alkoxy group, although a hydroxyl group can also be used. When the polymer is PEG, for example, it is preferred to use a methoxy-PEG (commonly referred to as mPEG), which is a linear form of PEG wherein one terminus of the polymer has a methoxy ($—OCH_3$) group, while the other terminus is a hydroxyl or other functional group that can be optionally chemically modified.

In one form useful in the present invention, free or unbound PEG is a linear polymer terminated at each end with hydroxyl groups:

$$HO—CH_2CH_2O—(CH_2C_2O)_n—CH_2CH_2—OH,$$

wherein (n) typically ranges from zero to about 4,000.

The above polymer, alpha-, omega-dihydroxylpoly(ethylene glycol), can be represented in brief form as HO-PEG-OH where it is understood that the -PEG- symbol can represent the following structural unit:

$$—CH_2CH_2O—(CH_2CH_2O)_n—CH_2CH_2—,$$

wherein (n) is as defined as above.

Another type of PEG useful in the present invention is methoxy-PEG-OH, or mPEG in brief, in which one terminus is the relatively inert methoxy group, while the other terminus is a hydroxyl group. The structure of mPEG is given below.

$$CH_3O—CH_2CH_2O—(CH_2CH_2O)_n—CH_2CH_2—OH$$

wherein (n) is as described above.

Multi-armed or branched PEG molecules, such as those described in U.S. Pat. No. 5,932,462, can also be used as the PEG polymer. For example, PEG can have the structure:

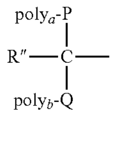

wherein:

$poly_a$ and $poly_b$ are PEG backbones (either the same or different), such as methoxy poly(ethylene glycol);

R" is a non-reactive moiety, such as H, methyl or a PEG backbone; and

P and Q are non-reactive linkages. In a one or more embodiments, the branched PEG polymer is methoxy poly (ethylene glycol) disubstituted lysine. Depending on the specific Factor IX moiety used, the reactive ester functional group of the disubstituted lysine may be further modified to form a functional group suitable for reaction with the target group within the Factor IX moiety.

In addition, the PEG can comprise a forked PEG. An example of a forked PEG is represented by the following structure:

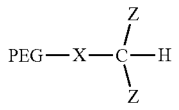

wherein X is a spacer moiety of one or more atoms and each Z is an activated terminal group linked to CH by a chain of atoms of defined length. International Application No. PCT/US99/05333, discloses various forked PEG structures capable of use in one or more embodiments of the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages (such as a hydrolytically degradable linkage) in the polymer, including any of the above described polymers. For example, PEG can be prepared with ester linkages in the polymer that are subject to hydrolysis. As shown below, this hydrolysis results in cleavage of the polymer into fragments of lower molecular weight:

$$\text{-PEG-}CO_2\text{-PEG-}+H_2O \rightarrow \text{-PEG-}CO_2H+HO\text{-PEG-}$$

Other hydrolytically degradable linkages, useful as a degradable linkage within a polymer backbone, include: carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

Such optional features of the polymer conjugate, i.e., the introduction of one or more degradable linkages into the polymer chain, may provide for additional control over the final desired pharmacological properties of the conjugate upon administration. For example, a large and relatively inert conjugate (e.g., having one or more high molecular weight PEG chains attached to a Factor IX moiety, for example, one or more PEG chains having a molecular weight greater than about 10,000, wherein the conjugate possesses essentially no bioactivity) may be administered, which is hydrolyzed to generate a bioactive conjugate possessing a portion of the original PEG chain. In this way, the properties of the conjugate can be more effectively tailored to balance the bioactivity of the conjugate over time.

Those of ordinary skill in the art will recognize that the foregoing discussion concerning substantially water-soluble polymer segments is by no means exhaustive and is merely illustrative, and that all polymeric materials having the qualities described above are contemplated. As used herein, the term "polymeric reagent" generally refers to an entire molecule, which can comprise a water-soluble polymer segment and a functional group.

Conjugates

As described above, a conjugate of the invention comprises a water-soluble polymer covalently attached (either directly or through a spacer moiety) to a Factor IX moiety. Typically, for any given conjugate, there will be one to four water-soluble polymers covalently attached to a Factor IX moiety (wherein for each water-soluble polymer, the water soluble polymer can be attached either directly to the Factor IX moiety or through a spacer moiety). In some instances, however, the conjugate may have 1, 2, 3, 4, 5, 6, 7, 8 or more water-soluble polymers individually attached to a Factor IX moiety. In addition, the conjugate may include not more than 8 water-soluble polymers individually attached to a Factor IX moiety, not more than 7 water-soluble polymers individually attached to a Factor IX moiety, not more than 6 water-soluble polymers individually attached to a Factor IX moiety, not more than 5 water-soluble polymers individually attached to a Factor IX moiety, not more than 4 water-soluble polymers individually attached to a Factor IX moiety, not more than 3 water-soluble polymers individually attached to a Factor IX moiety, and not more than 2 water-soluble polymers individually attached to a Factor IX moiety.

The particular linkage between the Factor IX moiety and the polymer (or the spacer moiety that is attached to the polymer) depends on a number of factors. Such factors include, for example, the particular linkage chemistry employed, the particular Factor IX moiety, the available functional groups within the Factor IX moiety (either for attachment to a polymer or conversion to a suitable attachment site), the possible presence of additional reactive functional groups within the Factor IX moiety, and the like.

In one or more embodiments of the invention, the linkage between the Factor IX moiety and the polymer (or the spacer moiety that is attached to the polymer) is a hydrolytically stable linkage, such as an amide, urethane (also known as carbamate), amine, thioether (also known as sulfide), or urea (also known as carbamide). In one or more embodiments, the linkage does not result from reaction of the polymeric reagent bearing triazine, acetyl, hydrazine, diazonium, amino, or succinimidyl ester functional group with the Factor IX moiety. In some cases, it is preferred that the linkage is not a carbamate linkage and not a carbamide linkage, and furthermore, that no linkage is formed based on the reaction of a polymer derivative bearing an isocyanate or isothiocyanate species to a Factor IX moiety. Again, a preferred hydrolytically stable linkage is an amide. An amide can be readily prepared by reaction of a carboxyl group contained within the Factor IX moiety (e.g., the terminal carboxyl of a peptidic moiety having Factor IX activity) with an amino-terminated polymer.

In one or more embodiments of the invention, the linkage between the Factor IX moiety and the polymer (or the spacer moiety that is attached to the polymer) is a degradable linkage. In this way, the linkage of the water-soluble polymer (and any spacer moiety) is "cleavable." That is, the water-soluble polymer (and any spacer moiety) cleaves (either through hydrolysis, enzymatic processes, or otherwise), thereby resulting in the native or unconjugated Factor IX moiety. Preferably, cleavable linkages result in the polymer (and any spacer moiety) detaching from the Factor IX moiety in vivo without leaving any fragment of the water-soluble polymer (and any spacer moiety). Exemplary degradable linkages include carbonate, carboxylate ester, phosphate ester, thiolester, anhydrides, acetals, ketals, acyloxyalkyl ether, imines, and orthoesters. Such linkages can be readily prepared by appropriate modification of either the Factor IX moiety (e.g., the carboxyl group C terminus of the protein or a side chain hydroxyl group of an amino acid such as serine or threonine contained within the protein) and/or the polymeric reagent using coupling methods commonly employed in the art. Most preferred, however, are hydrolyzable linkages that are readily formed by reaction of a suitably activated polymer with a non-modified functional group contained within the moiety having Factor IX activity.

With regard to linkages, in one more embodiments of the invention, a conjugate is provided, comprising a Factor IX moiety covalently attached at an amino acid residue, either directly or through a spacer moiety comprised of one or more atoms, to a water-soluble polymer, wherein the amino acid residue is not attached, either directly or through the spacer moiety, via a $CH_2$—C(O)—O—, —N(H)—C(O)$CH_2$—O—, —C(O)—N(H)—, —N(H)—C(O)—$CH_2$—O—, —C(O)—$CH_2$—O—, —C(O)—$CH_2$—$CH_2$—C(O)—O—, diazo, or triazine linkage.

The conjugates (as opposed to an unconjugated Factor IX moiety) may or may not possess a measurable degree of Factor IX activity. That is to say, a conjugate in accordance with the invention will possesses anywhere from about 0% to about 100% or more of the bioactivity of the unmodified parent Factor IX moiety. Preferably, compounds possessing little or no Factor IX activity typically contain a hydrolyzable linkage connecting the polymer to the moiety, so that regardless of the lack of activity in the conjugate, the active parent molecule (or a derivative thereof having Factor IX activity) is released upon aqueous-induced cleavage of the linkage. Such activity may be determined using a suitable in-vivo or in-vitro model, depending upon the known activity of the particular moiety having Factor IX activity employed.

Optimally, cleavage of each water-soluble polymer portion is facilitated through the use of physiologically cleavable and/or enzymatically degradable linkages such as urethane, amide, carbonate or ester-containing linkages. In this way, clearance of the conjugate [via cleavage of individual water-soluble polymer(s)] can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer-Factor IX conjugates with different polymer weights and cleavable functional groups, and then obtaining the clearance profile for each conjugate by administering the conjugate to a patient and taking periodic blood and/or urine sampling. Once a series of clearance profiles have been obtained for each tested conjugate, a conjugate having the desired clearance can be identified.

For conjugates possessing a hydrolytically stable linkage that couples the Factor IX moiety to the polymer, the conjugate will typically possess a measurable degree of Factor IX activity. For instance, such conjugates are typically characterized as having a bioactivity satisfying one or more of the following percentages relative to that of the unconjugated Factor IX moiety: at least about 2%, at least about 5%, at least about 10%, at least about 15%, at least about 25%, at least about 30%, at least about 40%, at least about 50%, at least about 60%, at least about 80%, at least about 85%, at least about 90%, at least about 95%, at least about 97%, at least about 100%, and more than 105% (when measured in a suitable model, such as those presented here and/or well known in the art). Preferably, conjugates having a hydrolytically stable linkage (e.g., an amide linkage) will possess at least some degree of the bioactivity of the unmodified parent Factor IX moiety.

Exemplary conjugates will now be described. The Factor IX moiety is expected to share (at least in part) an amino acid sequence similar or related to native Factor IX. Thus, while reference will be made to specific locations or atoms within the native Factor IX protein, such a reference is for convenience only and one having ordinary skill in the art will be able to readily determine the corresponding location or atom in other moieties having Factor IX activity. In particular, the description provided herein for native Factor IX is often applicable to Factor IXa, as well as fragments, deletion variants, substitution variants or addition variants of any of the foregoing.

Amino groups on Factor IX moieties can provide a point of attachment between the Factor IX moiety and the water-soluble polymer. Native Factor IX comprises 27 lysine residues, each having an ϵ-amino group that may be available for conjugation, as well as one amino terminus. Thus, exemplary attachment points of such Factor IX moieties include attachment at an amino acid (through the amine-containing side chain of lysine) at any one or more of positions 39, 45, 51, 68, 89, 109, 127, 137, 146, 168, 189, 234, 247, 260, 274, 293, 311, 339, 347, 362, 387, 438, 440, 446, 455, 457, and 459. Further, the N-terminal amine of any protein having Factor IX activity can also serve as a point of attachment.

There are a number of examples of suitable water-soluble polymeric reagents useful for forming covalent linkages with available amines of a Factor IX moiety. Specific examples, along with the corresponding conjugates, are provided in Table 1, below. In the table, the variable (n) represents the number of repeating monomeric units and "—NH—F9" represents the Factor IX moiety following conjugation to the water-soluble polymer. While each polymeric portion [e.g., $(OCH_2CH_2)_n$ or $(CH_2CH_2O)_n$] presented in Table 1 terminates in a "$CH_3$" group, other groups (such as H and benzyl) can be substituted therefor.

TABLE 1

Amine-Specific Polymeric Reagents and the Factor IX Moiety Conjugate Formed Therefrom

| Polymeric Reagent | Corresponding Conjugate |
|---|---|
| 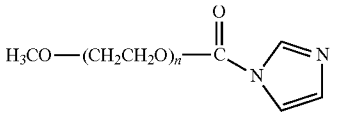 mPEG-Oxycarbonylimidazole Derivative | 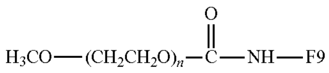 Carbamate Linkage |
| 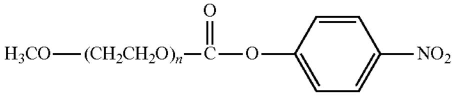 mPEG Nitrophenyl Derivative | 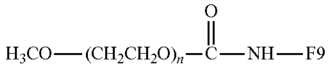 Carbamate Linkage |
| 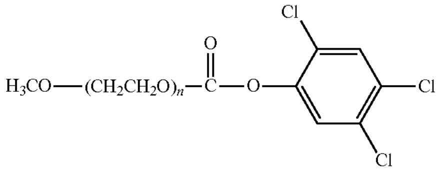 mPEG-Trichlorophenyl Carbonates | 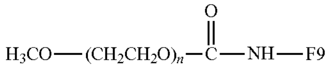 Carbamate Linkage |
| 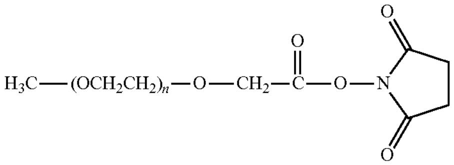 mPEG-Succinimidyl Derivative | 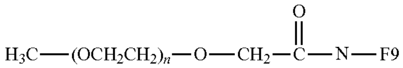 Amide Linkage |
| 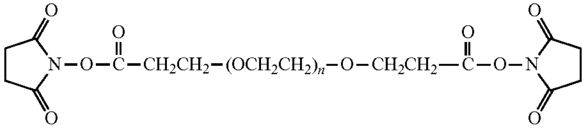 Homobifunctional PEG-Succinimidyl Derivative | 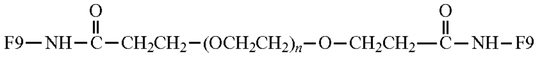 Amide Linkages |

TABLE 1-continued
| Amine-Specific Polymeric Reagents and the Factor IX Moiety Conjugate Formed Therefrom | |
|---|---|
| Polymeric Reagent | Corresponding Conjugate |
| 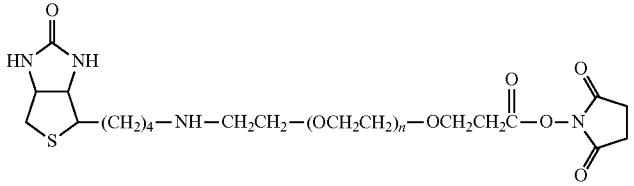 Heterobifunctional PEG-Succinimidyl Derivative | 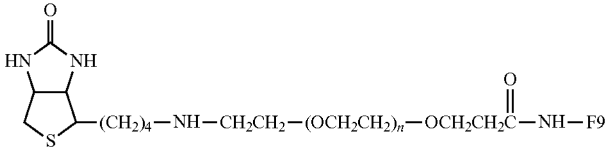 Amide Linkage |
| 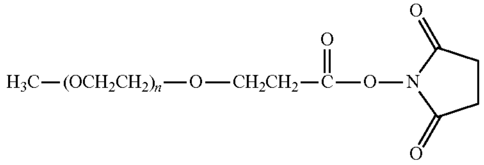 mPEG-Succinimidyl Derivative | 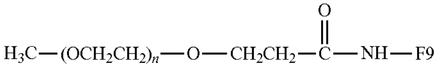 Amide Linkage |
| 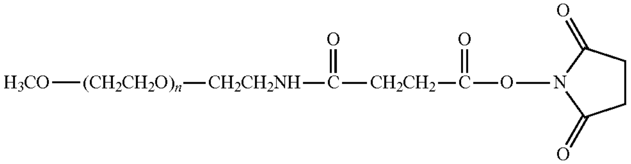 mPEG-Succinimdyl Derivative | 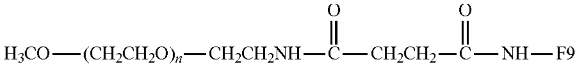 Amide Linkage |
| 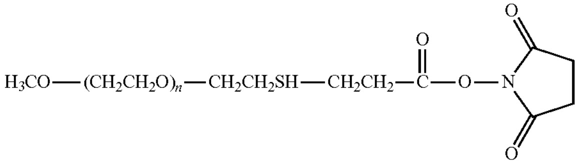 mPEG Succinimidyl Derivative | 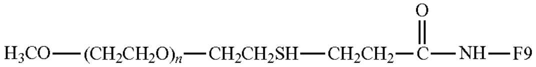 Amide Linkage |

TABLE 1-continued
| Amine-Specific Polymeric Reagents and the Factor IX Moiety Conjugate Formed Therefrom | |
|---|---|
| Polymeric Reagent | Corresponding Conjugate |
| 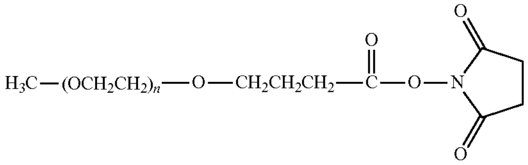 mPEG-Succinimidyl Derivative | 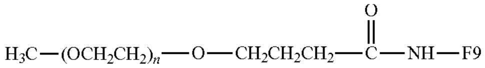 Amide Linkage |
| 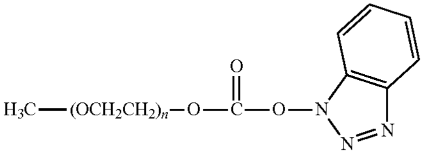 mPEG-Benzotriazole Carbonate Derivative | 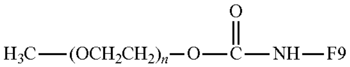 Carbamate Linkage |
| 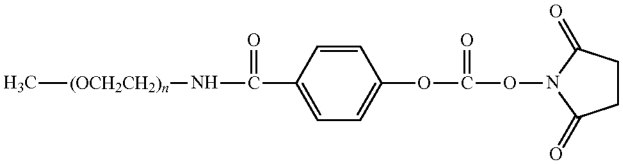 mPEG-Succinimidyl Derivative | 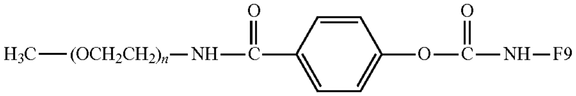 Carbamate Linkage |
| 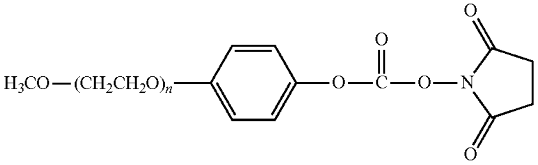 mPEG-Succinimidyl Derivative | 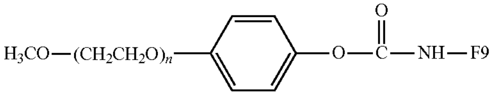 Amide Linkage |

TABLE 1-continued
| Amine-Specific Polymeric Reagents and the Factor IX Moiety Conjugate Formed Therefrom | |
|---|---|
| Polymeric Reagent | Corresponding Conjugate |
| 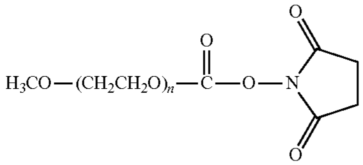 mPEG Succinimidyl Derivative | 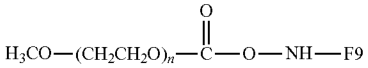 Amide Linkage |
| 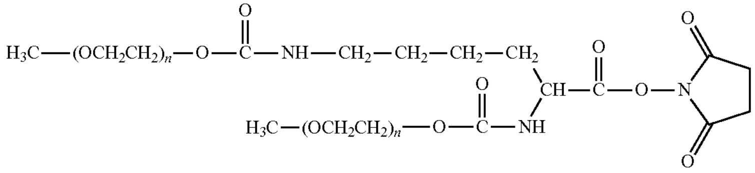 Branched mPEG2-N-Hydroxysuccinimide Derivative | 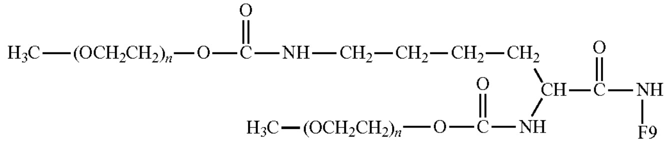 Amide Linkage |
| 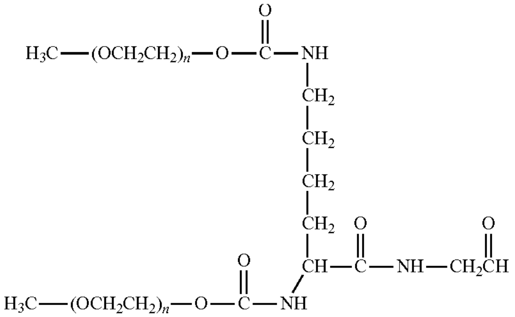 Branched mPEG2-Aldehyde Derivative | 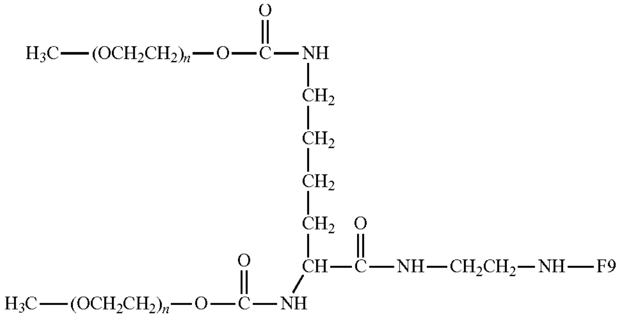 Secondary Amine Linkage |

TABLE 1-continued
Amine-Specific Polymeric Reagents and the Factor IX Moiety Conjugate Formed Therefrom
| Polymeric Reagent | Corresponding Conjugate |
|---|---|
| 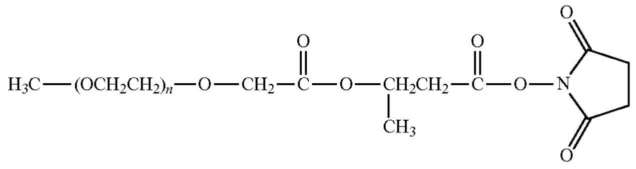 mPEG-Succinimidyl Derivative | 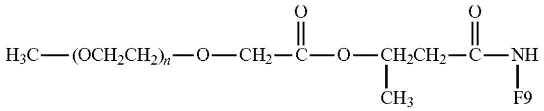 Amide Linkage |
| 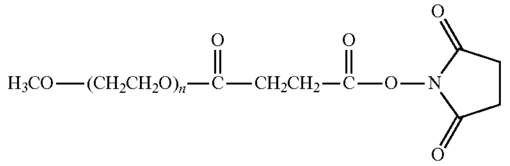 mPEG-Succinimidyl Derivative | 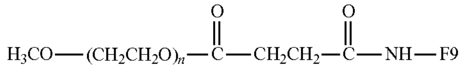 Amide Linkage |
| 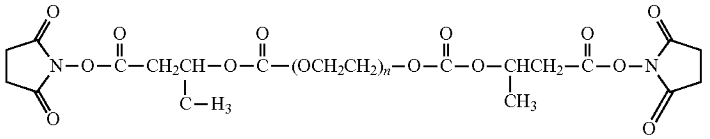 Homobifunctional PEG-Succinimidyl Derivative | 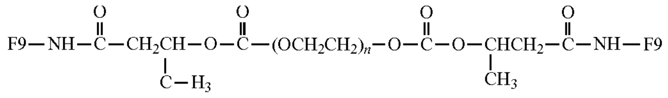 Amide Linkages |
| 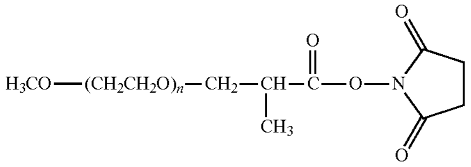 mPEG-Succinimidyl Derivative | 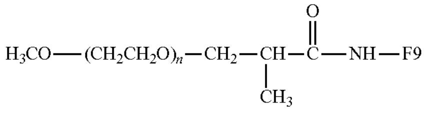 Amide Linkages |

TABLE 1-continued

| Amine-Specific Polymeric Reagents and the Factor IX Moiety Conjugate Formed Therefrom | |
| --- | --- |
| Polymeric Reagent | Corresponding Conjugate |
| 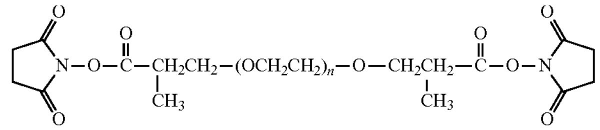 Homobifunctional PEG-Succinimidyl Propionate Derivative | 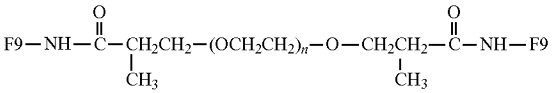 Amide Linkages |
| 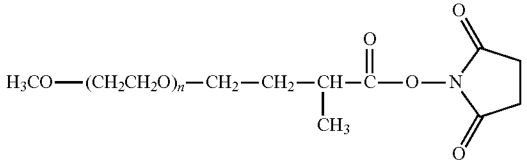 mPEG-Succinimidyl Derivative | 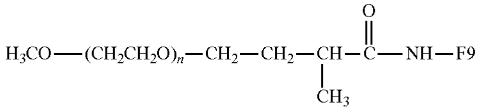 Amide Linkage |
| 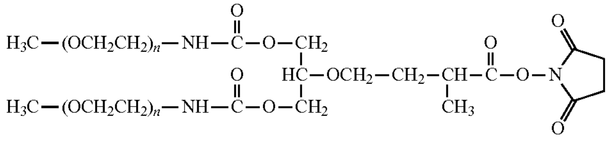 Branched mPEG2-N-Hydroxysuccinimide Derivative | 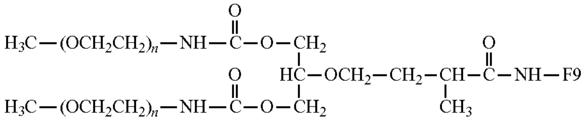 Amide Linkage |
| 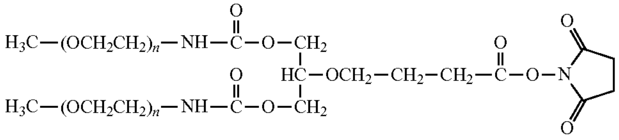 Branched mPEG2-N-Hydroxysuccinimide Derivative | 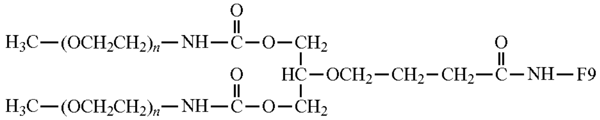 Amide Linkage |
| 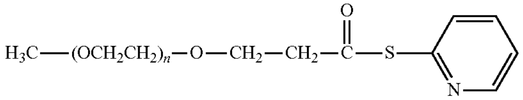 mPEG-Thioester Derivative | 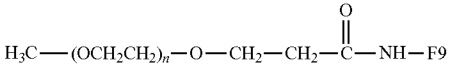 Amide Linkage (typically to Factor IX moiety having an N-terminal cysteine or histidine) |

TABLE 1-continued

Amine-Specific Polymeric Reagents and the Factor IX Moiety Conjugate Formed Therefrom

| Polymeric Reagent | Corresponding Conjugate |
| --- | --- |
| 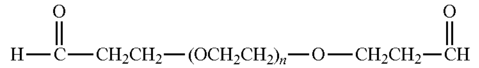<br>Homobifunctional PEG Propionaldehyde Derivative | 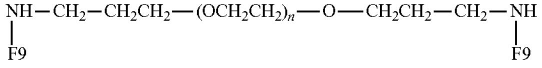<br>Secondary Amine Linkages |
| 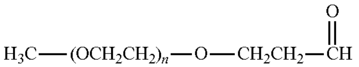<br>mPEG Propionaldehyde Derivative | $H_3C—(OCH_2CH_2)_n—O—CH_2CH_2—CH_2—NH—F9$<br>Secondary Amine Linkage |
| 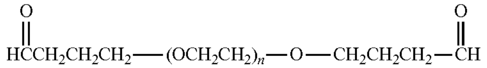<br>Homobifunctional PEG Butyraldehyde Derivative | 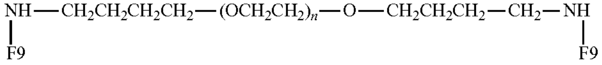<br>Secondary Amine Linkages |
| 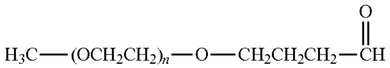<br>mPEG Butryaldehyde Derivative | $H_3C—(OCH_2CH_2)_n—O—CH_2CH_2CH_2—CH_2—NH—F9$<br>Secondary Amine Linkage |
| 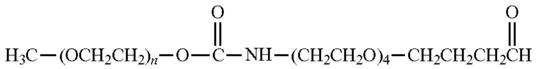<br>mPEG Butryaldehyde Derivative | 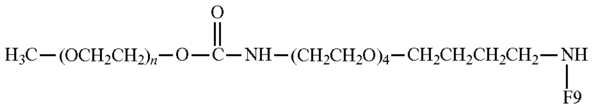<br>Secondary Amine Linkage |
| 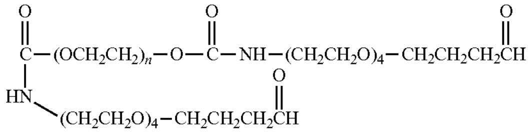<br>Homobifunctional PEG Butryaldehyde Derivative | 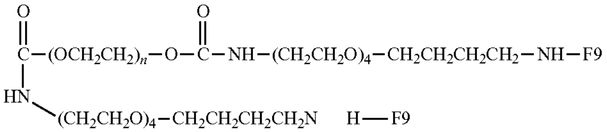<br>Secondary Amine Linkates |

TABLE 1-continued

| Amine-Specific Polymeric Reagents and the Factor IX Moiety Conjugate Formed Therefrom | |
|---|---|
| Polymeric Reagent | Corresponding Conjugate |
| 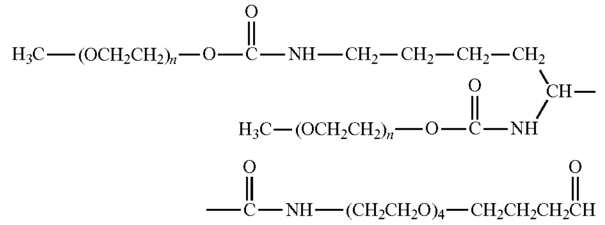<br>Branched mPEG2 Butyraldehyde Derivative | 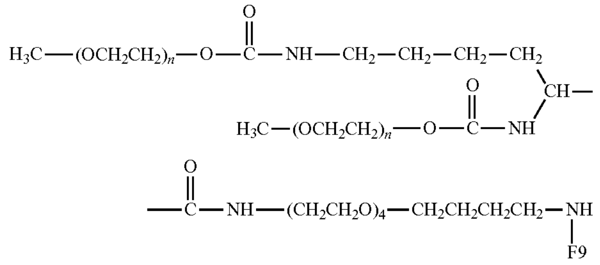<br>Secondary Amine Linkage |
| 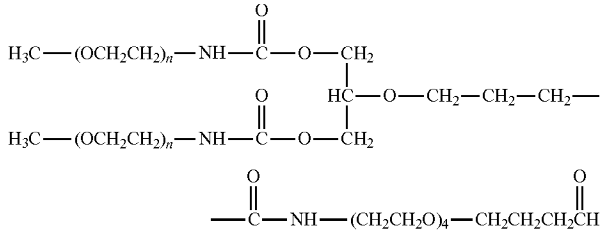<br>Branched mPEG2 Butyraldehyde Derivative | 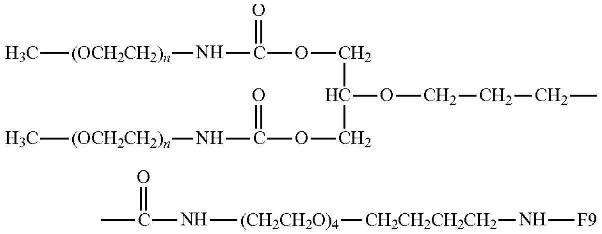<br>Secondary Amine Linkage |
| 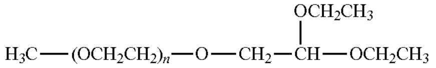<br>mPEG Acetal Derivative | $H_3C—(OCH_2CH_2)_n—O—CH_2CH_2—NH—F9$<br>Secondary Amine Linkage |
| 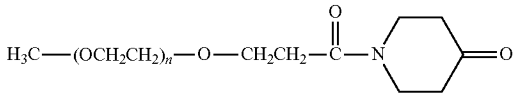<br>mPEG Piperidone Derivative | 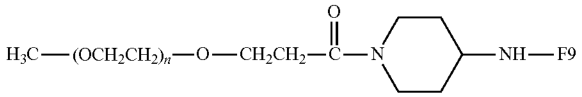<br>Secondary Amine Linkage<br>(to a secondary carbon) |

TABLE 1-continued

| Amine-Specific Polymeric Reagents and the Factor IX Moiety Conjugate Formed Therefrom | |
|---|---|
| Polymeric Reagent | Corresponding Conjugate |
| 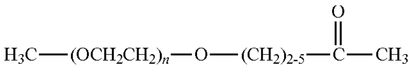<br>mPEG Methylketone Derivative | 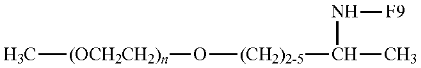<br>secondary amine linkage<br>(to a secondary carbon) |
| 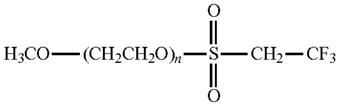<br>mPEG tresylate | $H_3CO—(CH_2CH_2O)_n—CH_2CH_2—NH—F9$<br>Secondary Amine Linkage |
| 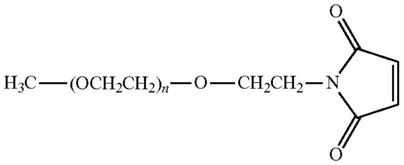<br>mPEG Maleimide Derivative<br>(under certain reaction conditions such as pH > 8) | 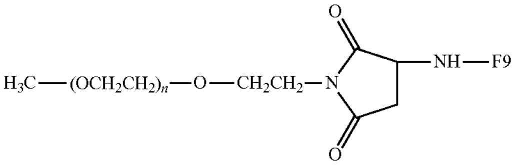<br>Secondary Amine Linkage |
| 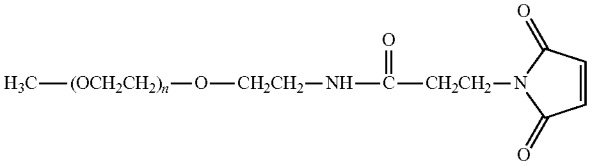<br>mPEG Maleimide Derivative<br>(under certain reaction conditions such as pH > 8) | 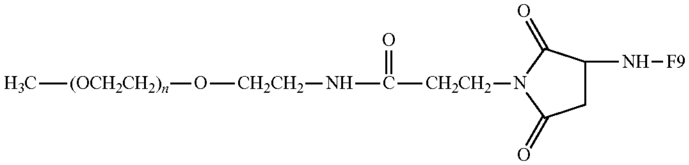<br>Secondary Amine Linkage |
| 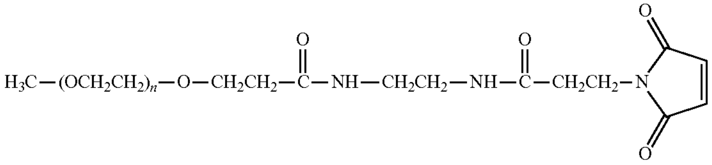<br>mPEG Maleimide Derivative<br>(under certain reaction conditions such as pH > 8) | 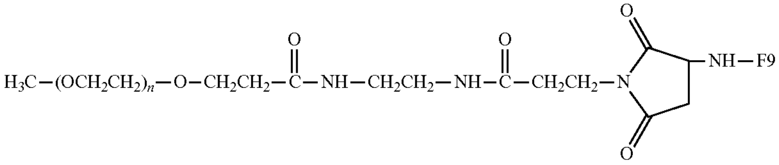<br>Secondary Amine Linkage |

TABLE 1-continued
| Amine-Specific Polymeric Reagents and the Factor IX Moiety Conjugate Formed Therefrom | |
|---|---|
| Polymeric Reagent | Corresponding Conjugate |
| 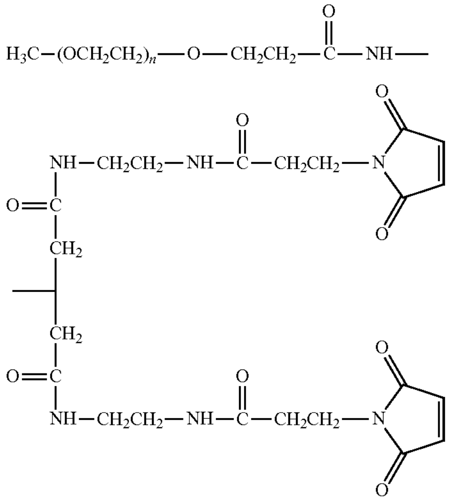 mPEG Forked Maleimide Derivative (under certain reaction conditions such as pH > 8) | 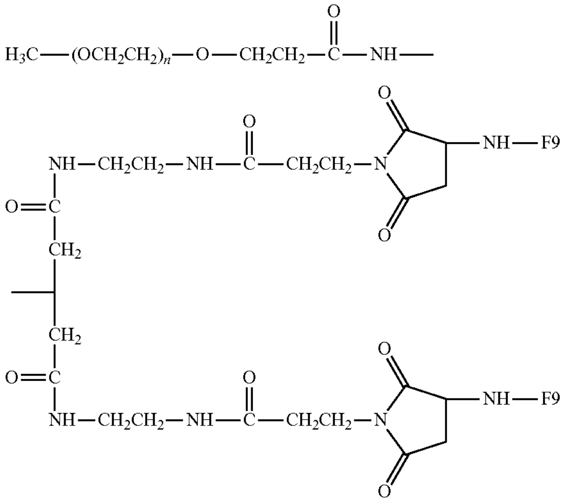 Secondary Amine Linkages |

TABLE 1-continued
| Amine-Specific Polymeric Reagents and the Factor IX Moiety Conjugate Formed Therefrom | |
|---|---|
| Polymeric Reagent | Corresponding Conjugate |
| 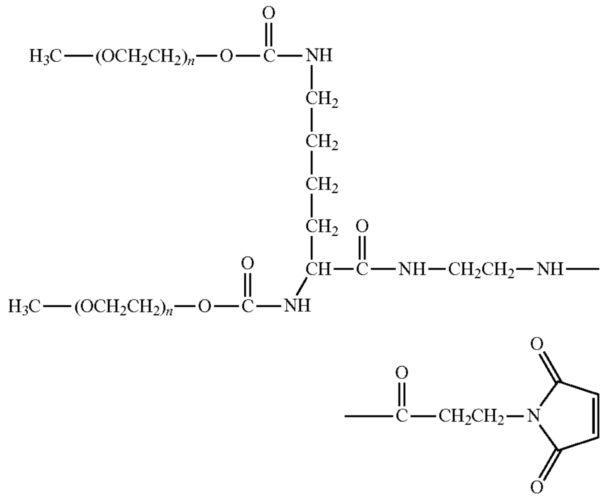 branched mPEG2 Maleimide Derivative (under certain reaction conditions such as pH > 8) | 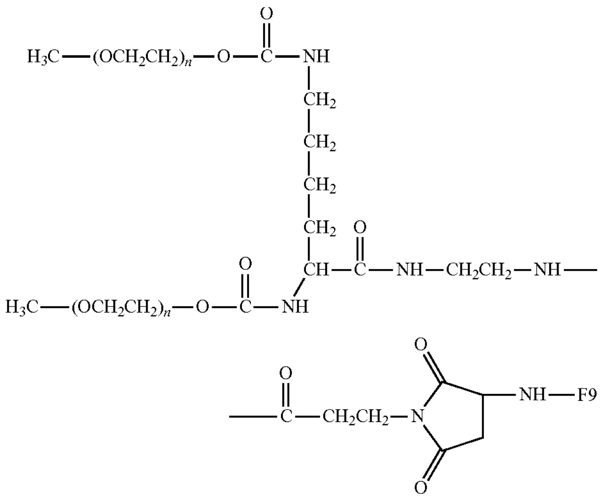 Secondary Amine Linkage |

Conjugation of a polymeric reagent to an amine group of a Factor IX moiety can be accomplished by a variety of techniques. In one approach, a Factor IX moiety can be conjugated to a polymeric reagent functionalized with a succinimidyl derivative (or other activated ester group, wherein approaches similar to those described for a succinimidyl derivative can be used for other activated ester group-containing polymeric reagents). In this approach, the polymeric reagent bearing a succinimidyl group can be attached to the Factor IX moiety in aqueous media at a pH of 7.0 to 9.0, although different reaction conditions (e.g., a lower pH such as 6 to 7, or different temperatures and/or less than 15° C.) can result in the attachment of a polymer to a different location on the Factor IX moiety. In addition, an amide linkage can be formed by reacting an amine-terminated non-peptidic, water-soluble polymer with a Factor IX moiety bearing an aldehyde or an activated carboxylic acid group.

An exemplary conjugate comprises the following structure

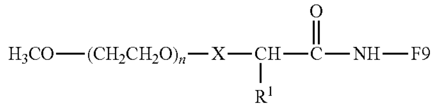

wherein:

(n) is an integer having a value of from 2 to 3400;

X is a spacer moiety, preferably one of methylene ("$-CH_2-$"), ethylene ("$-CH_2CH_2-$") and propylene ("$-CH_2CH_2CH_2-$");

$R^1$ is an organic radical, preferably H or methyl ("$-CH_3$"); and

F9 is a Factor IX moiety.

Typical of another approach useful for conjugating the Factor IX moiety to a polymeric reagent is the use of a reductive amination reaction to conjugate a primary amine of a Factor IX moiety with a polymer functionalized with a ketone, aldehyde or a hydrated form thereof (e.g., ketone hydrate and aldehyde hydrate). In this approach, the primary amine from the Factor IX moiety reacts with the carbonyl group of the aldehyde or ketone (or the corresponding hydroxy-containing group of a hydrated aldehyde or ketone), thereby forming a Schiff base. The Schiff base, in turn, can then be reductively converted to a stable conjugate through use of a reducing agent such as sodium borohydride. Selective reactions (e.g., at the N-terminus are possible) are possible, particularly with a polymer functionalized with a ketone or an alpha-methyl branched aldehyde and/or under specific reaction conditions (e.g., reduced pH).

Carboxyl groups represent another functional group that can serve as a point of attachment on the Factor IX moiety. Structurally, the conjugate will comprise the following:

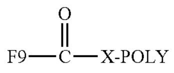

where F9 and the adjacent carbonyl group corresponds to the carboxyl-containing Factor IX moiety, X is a spacer moiety, preferably a heteroatom selected from O, N(H), and S, and POLY is a water-soluble polymer such as PEG, optionally terminating in an end-capping moiety.

The C(O)—X linkage results from the reaction between a polymeric derivative bearing a terminal functional group and a carboxyl-containing Factor IX moiety. As discussed above, the specific linkage will depend on the type of functional group utilized. If the polymer is end-functionalized or "activated" with a hydroxyl group, the resulting linkage will be a carboxylic acid ester and X will be 0. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linkage structure.

Polymeric reagents containing a hydrazide moiety are also useful for conjugation at a carbonyl. To the extent that the Factor IX moiety does not contain a carbonyl moiety, a carbonyl moiety can be introduced by reducing any carboxylic acids (e.g., the C-terminal carboxylic acid) and/or by providing glycosylated or glycated (wherein the added sugars have a carbonyl moiety) versions of the Factor IX moiety. Specific examples of polymeric reagents comprising a hydrazide moiety, along with the corresponding conjugates, are provided in Table 2, below. In addition, any polymeric reagent comprising an activated ester (e.g., a succinimidyl group) can be converted to contain a hydrazide moiety by reacting the polymeric reagent comprising the activated ester with hydrazine ($NH_2-NH_2$) or tert-butyl carbazate [$NH_2NHCO_2C(CH_3)_3$]. In the table, the variable (n) represents the number of repeating monomeric units and "=C—F9" represents the Factor IX moiety following conjugation to the polymeric reagent. Optionally, the hydrazone linkage can be reduced using a suitable reducing agent. While each polymeric portion [e.g., $(OCH_2CH_2)_n$ or $(CH_2CH_2O)_n$] presented in Table 1 terminates in a "$CH_3$" group, other groups (such as H and benzyl) can be substituted therefor.

TABLE 2

| Carboxyl-Specific Polymeric Reagents and the Factor IX Moiety Conjugate Formed Therefrom | |
|---|---|
| Polymeric Reagent | Corresponding Conjugate |
| 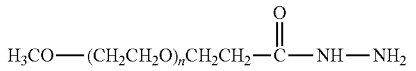 mPEG-Hydrazine Derivative | 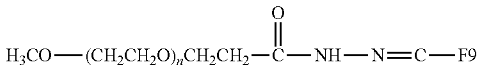 Hydrazone Linkage |
| 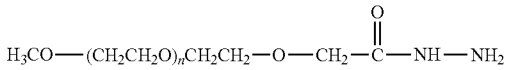 mPEG-Hydrazine Derivative | 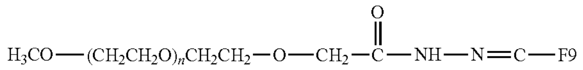 Hydrazone Linkage |

TABLE 2-continued

| Carboxyl-Specific Polymeric Reagents and the Factor IX Moiety Conjugate Formed Therefrom | |
|---|---|
| Polymeric Reagent | Corresponding Conjugate |
| 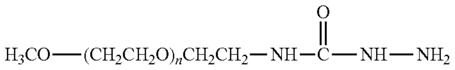 mPEG-Hydrazine Derivative | 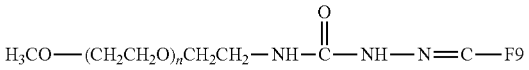 Hydrazone Linkage |
| 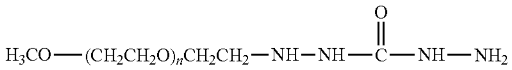 mPEG-Hydrazine Derivative | 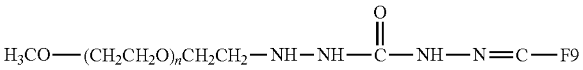 Hydrazone Linkage |
| 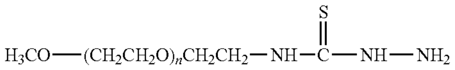 mPEG-Hydrazine Derivative | 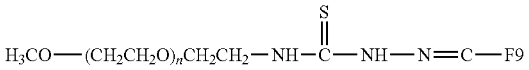 Hydrazone Linkage |
| 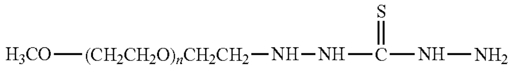 mPEG-Hydrazine Derivative | 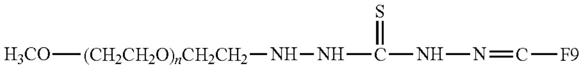 Hydrazone Linkage |
| 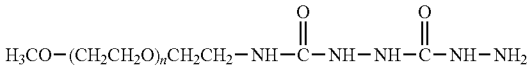 mPEG-Hydrazine Derivative | 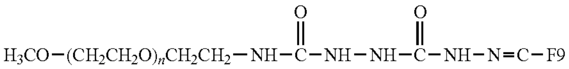 Hydrazone Linkage |
| 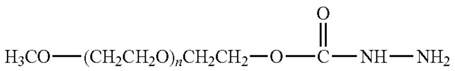 mPEG-Hydrazine Derivative | 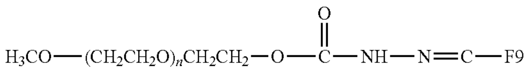 Hydrazone Linkage |

Thiol groups contained within the Factor IX moiety can serve as effective sites of attachment for the water-soluble polymer. In particular, cysteine residues provide thiol groups when the Factor IX moiety is a protein. The thiol groups in such cysteine residues can be reacted with an activated PEG that is specific for reaction with thiol groups, e.g., an N-maleimidyl polymer or other derivative, as described in U.S. Pat. No. 5,739,208 and in International Patent Publication No. WO 01/62827.

While not wishing to be bound by theory, it is believed that all of the cysteine residues within Factor IX participate in disulfide bonding. As a consequence, conjugation to a cysteine residue participating in disulfide bonding may disrupt the tertiary structure of Factor IX and potentially significantly decrease its overall activity. Thus, to the extent that any particular Factor IX moiety lacks a thiol group or disruption of disulfide bonds is to be avoided, it is possible to add a cysteine residue to the Factor IX moiety using conventional synthetic techniques. See, for example, the procedure described in International Patent Publication WO 90/12874 for adding cysteine residues, wherein such a procedure can be adapted for a Factor IX moiety. In addition, conventional genetic engineering processes can also be used to introduce a cysteine residue into the Factor IX moiety.

Specific examples, along with the corresponding conjugates, are provided in Table 3, below. In the table, the variable (n) represents the number of repeating monomeric units and "—S—F9" represents the Factor IX moiety following conjugation to the water-soluble polymer. While each polymeric portion [e.g., $(OCH_2CH_2)_n$ or $(CH_2CH_2O)_n$] presented in Table 3 terminates in a "$CH_3$" group, other groups (such as H and benzyl) can be substituted therefor.

TABLE 3
| Thiol-Specific Polymeric Reagents and he Factor IX Moiety Conjugate Formed Therefrom | |
|---|---|
| Polymeric Reagent | Corresponding Conjugate |
| 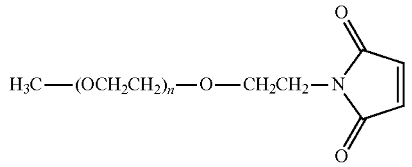 mPEG Maleimide Derivative | 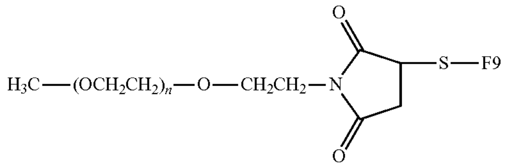 Thioether Linkage |
| 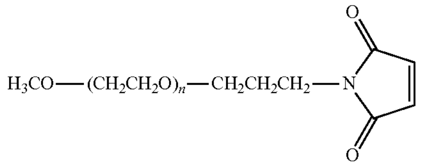 mPEG Maleimide Derivative | 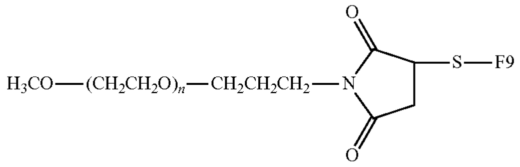 Thioether Linkage |
| 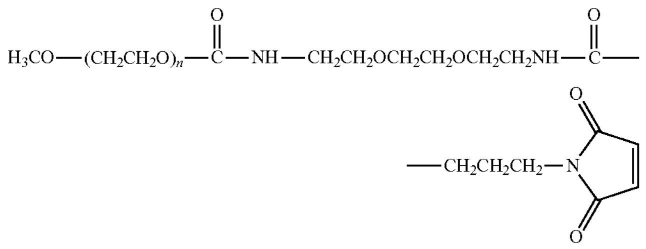 mPEG Maleimide Derivative | 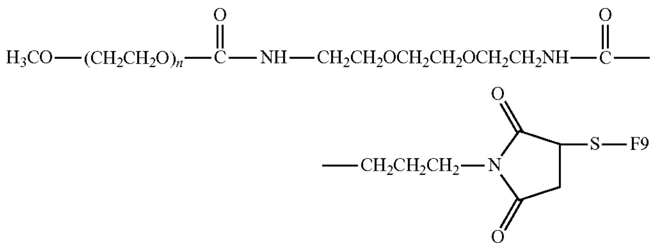 Thioether Linkage |

TABLE 3-continued
| Thiol-Specific Polymeric Reagents and he Factor IX Moiety Conjugate Formed Therefrom | |
|---|---|
| Polymeric Reagent | Corresponding Conjugate |
| 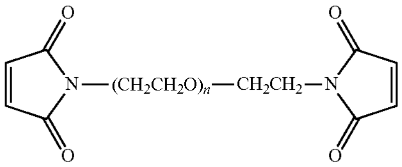<br>Homobifunctional mPEG Maleimide Derivative | 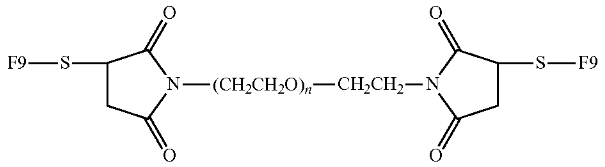<br>Thioether Linkages |
| 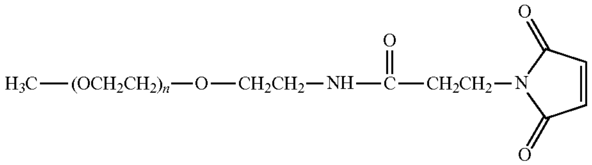<br>mPEG Maleimide Derivative | 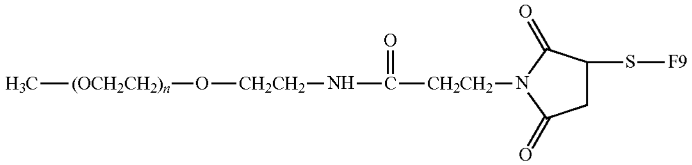<br>Thioether Linkage |
| 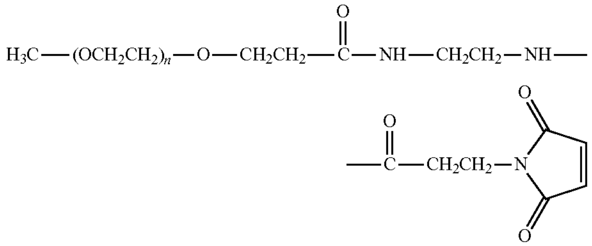<br>mPEG Maleimide Derivative | 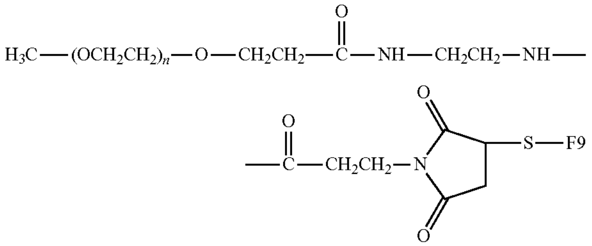<br>Thioether Linkage |

TABLE 3-continued
| Thiol-Specific Polymeric Reagents and he Factor IX Moiety Conjugate Formed Therefrom | |
|---|---|
| Polymeric Reagent | Corresponding Conjugate |
| 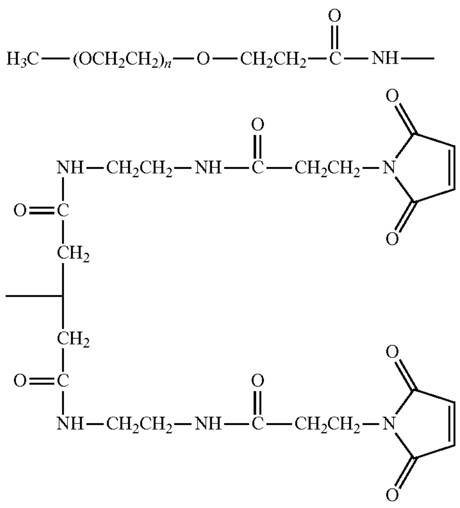 mPEG Forked Maleimide Derivative | 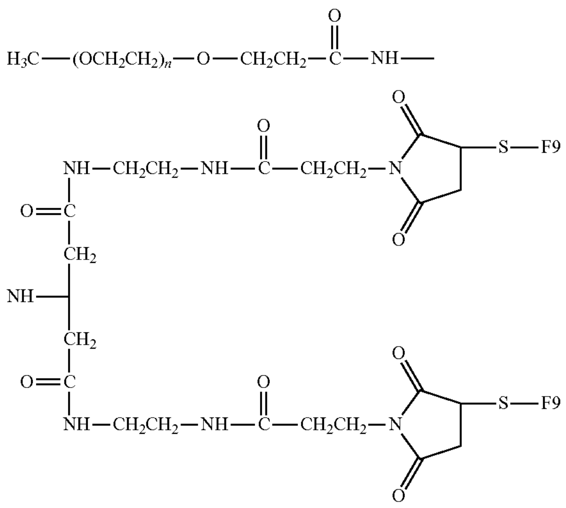 Thioether Linkage |

TABLE 3-continued
| Thiol-Specific Polymeric Reagents and he Factor IX Moiety Conjugate Formed Therefrom | |
|---|---|
| Polymeric Reagent | Corresponding Conjugate |
| 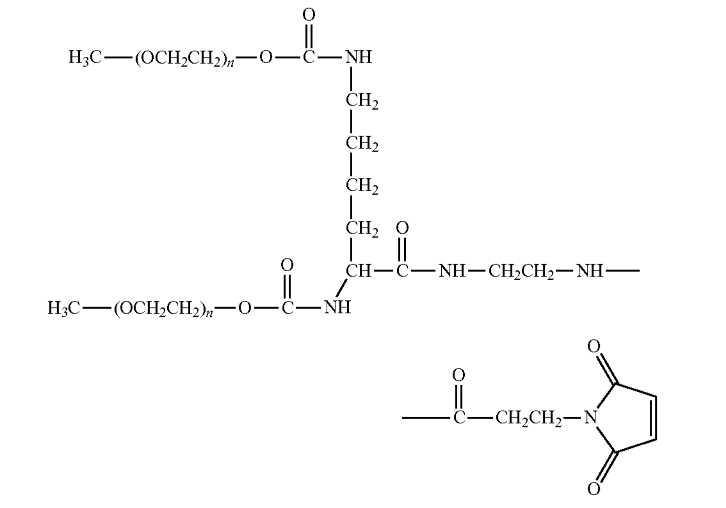 branched mPEG2 Maleimide Derivative | 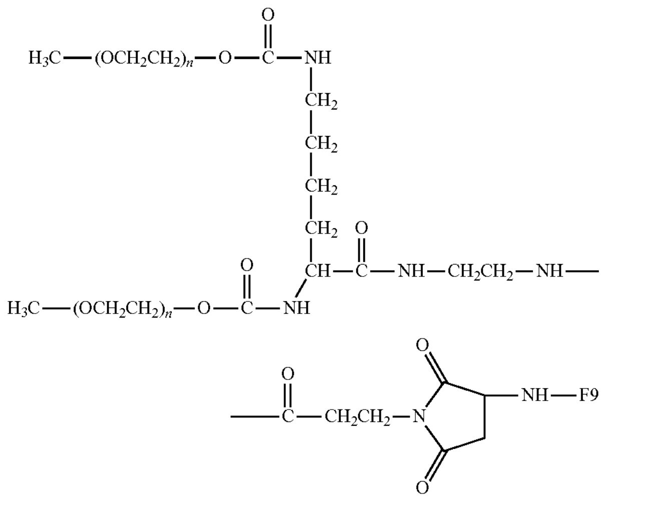 Thioether Linkage |
| 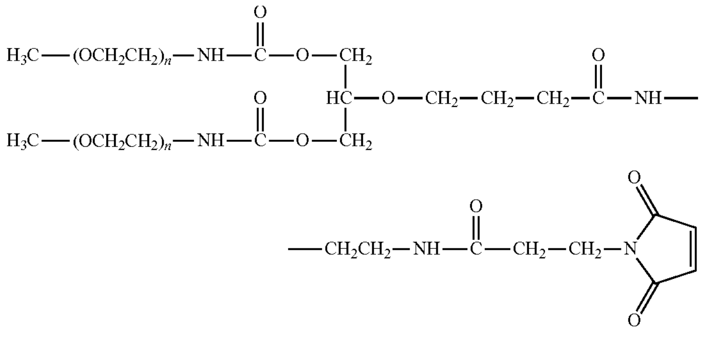 branched mPEG2 Maleimide Derivative | 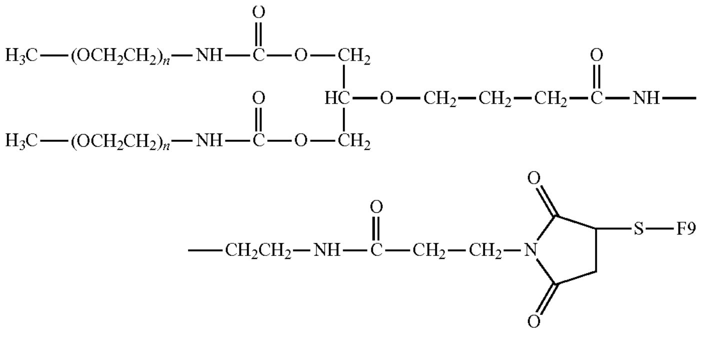 Thioether Linkage |

TABLE 3-continued
| Thiol-Specific Polymeric Reagents and he Factor IX Moiety Conjugate Formed Therefrom | |
|---|---|
| Polymeric Reagent | Corresponding Conjugate |
| 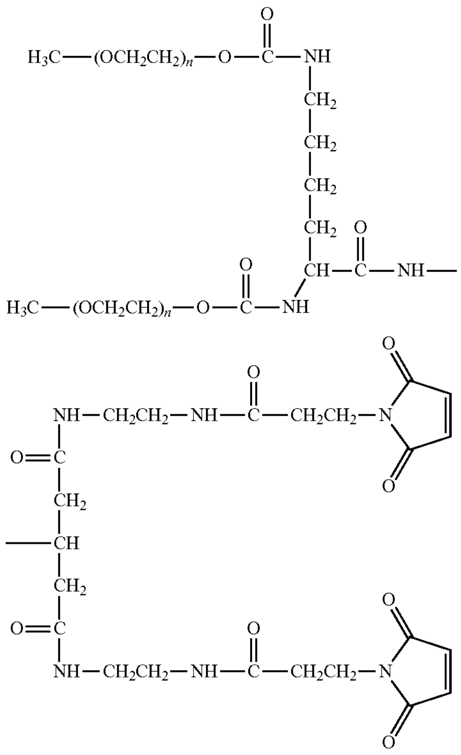 | 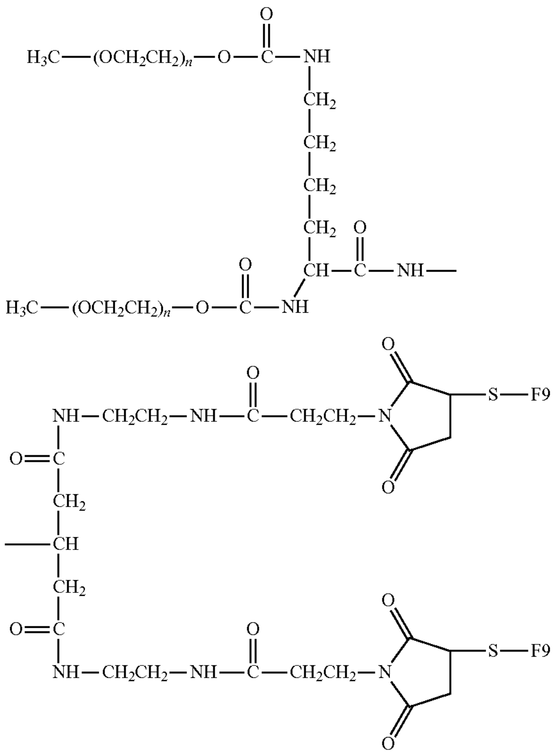 |
| Branched mPEG2 Forked Maleimide Derivative | Thioether Linkages |

TABLE 3-continued
| Thiol-Specific Polymeric Reagents and he Factor IX Moiety Conjugate Formed Therefrom | |
| --- | --- |
| Polymeric Reagent | Corresponding Conjugate |
| 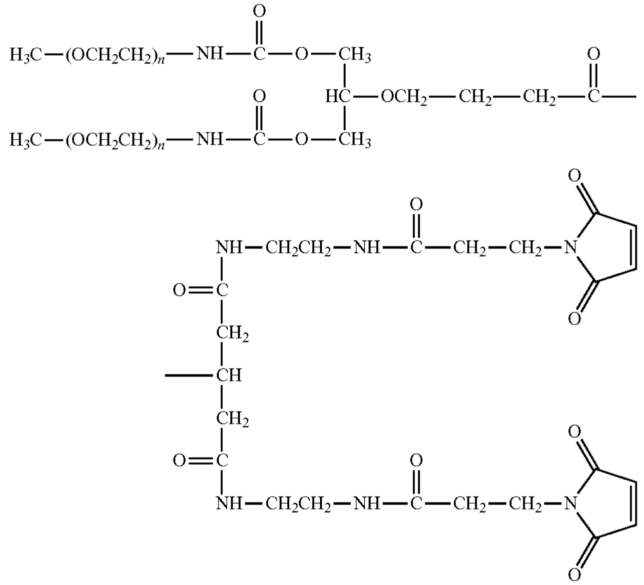 Branched mPEG2 Forked Maleimide Derivative | 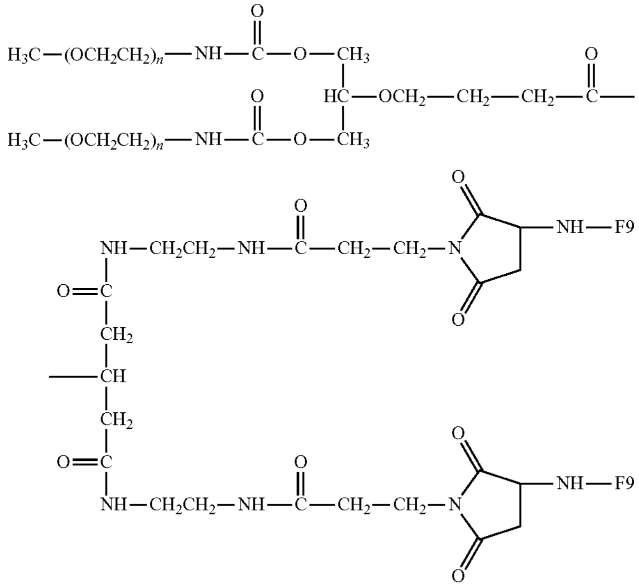 Thioether Linkages |
| 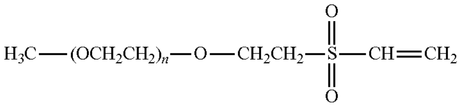 mPEG Vinyl Sulfone Derivative | 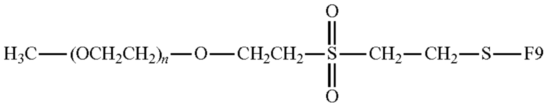 Thioether Linkage |
| 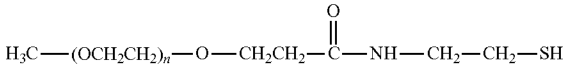 mPEG Thiol Derivative | 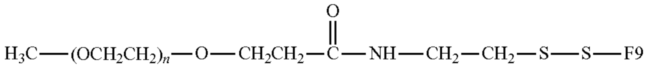 Disulfide Linkage |

TABLE 3-continued

| Thiol-Specific Polymeric Reagents and he Factor IX Moiety Conjugate Formed Therefrom | |
|---|---|
| Polymeric Reagent | Corresponding Conjugate |
| 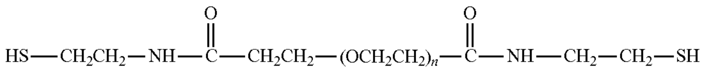 Homobifunctional PEG Thiol Derivative | 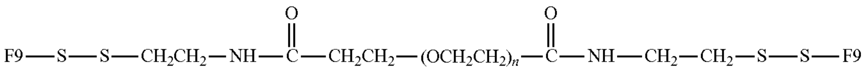 Disulfide Linkages |
| 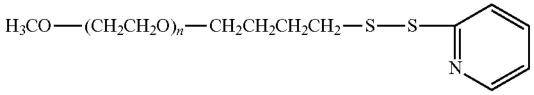 mPEG Disulfide Derivative | $H_3CO—(CH_2CH_2O)_n—CH_2CH_2CH_2CH_2—S—S—F9$ Disulfide Linkage |
| 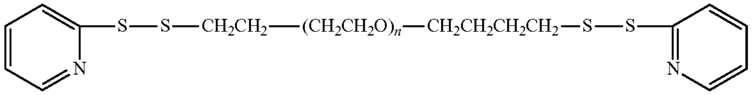 Homobifunctional PEG Disulfide Derivative | $F9—S—S—CH_2CH_2—(CH_2CH_2O)_n—CH_2CH_2CH_2CH_2—S—S—F9$ Disulfide Linkages |

With respect to conjugates formed from water-soluble polymers bearing one or more maleimide functional groups (regardless of whether the maleimide reacts with an amine or thiol group on the Factor IX moiety), the corresponding maleamic acid form(s) of the water-soluble polymer can also react with the Factor IX moiety. Under certain conditions (e.g., a pH of about 7-9 and in the presence of water), the maleimide ring will "open" to form the corresponding maleamic acid. The maleamic acid, in turn, can react with an amine or thiol group of a Factor IX moiety. Exemplary maleamic acid-based reactions are schematically shown below. POLY represents the water-soluble polymer, and F9 represents the Factor IX moiety.

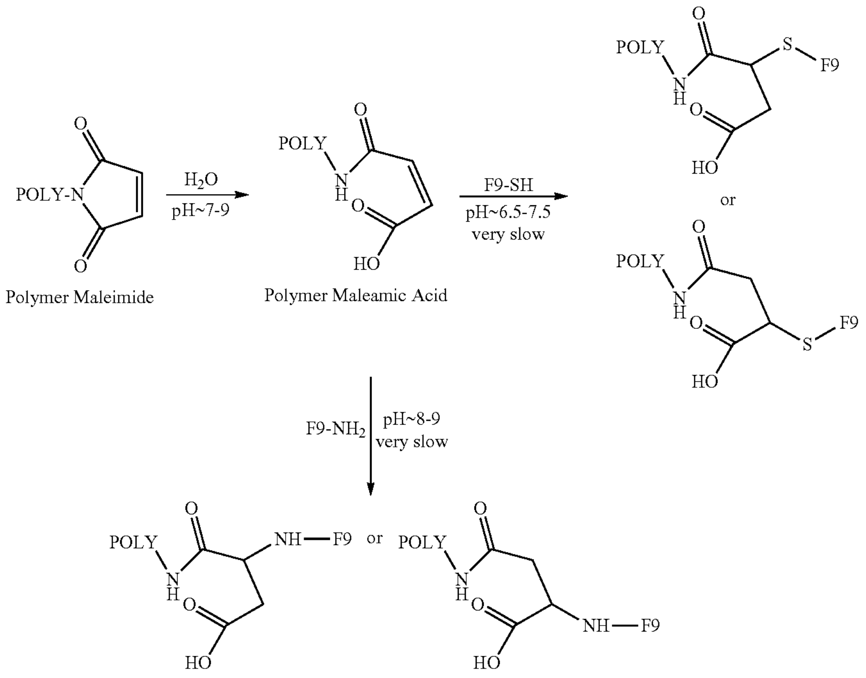

Polymer Maleimide
Polymer Maleamic Acid
or
or

A representative conjugate in accordance with the invention can have the following structure:

$POLY\text{-}L_{0,1}\text{-}C(O)Z\text{—}Y\text{—}S\text{—}S\text{—}F9$ wherein POLY is a water-soluble polymer, L is an optional linker, Z is a heteroatom selected from the group consisting of O, NH, and S, and Y is selected from the group consisting of $C_{2-10}$ alkyl, $C_{2-10}$ substituted alkyl, aryl, and substituted aryl, and F9 is a Factor IX moiety. Polymeric reagents that can be reacted with a Factor IX moiety and result in this type of conjugate are described in U.S. Patent Application Publication No. 2005/0014903.

With respect to polymeric reagents, those described here and elsewhere can be purchased from commercial sources (e.g., Nektar Therapeutics, Huntsville Ala.). In addition, methods for preparing the polymeric reagents are described in the literature.

The attachment between the Factor IX moiety and water-soluble polymer can be direct, wherein no intervening atoms are located between the Factor IX moiety can the polymer, or indirect, wherein one or more atoms are located between the Factor IX moiety and polymer. With respect to the indirect attachment, a "spacer moiety" serves as a link between the Factor IX moiety and the water-soluble polymer. The one or more atoms making up the spacer moiety can include one or more of carbon atoms, nitrogen atoms, sulfur atoms, oxygen atoms, and combinations thereof. The spacer moiety can comprise an amide, secondary amine, carbamate, thioether, and/or disulfide group. Nonlimiting examples of specific spacer moieties include those selected from the group consisting of —O—, —S—, —S—S—, —C(O)—, —C(O)—NH—, —NH—C(O)—NH—, —O—C(O)—NH—, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—C(O)—NH—$CH_2$—$CH_2$—, —$CH_2$—$CH_2$—$CH_2$—$CH_2$—C(O)—NH—, —C(O)—O—$CH_2$—, —$CH_2$—C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—NH—C(O)—$CH_2$—$CH_2$—, —C(O)—NH—$CH_2$—, —C(O)—NH—$CH_2$—$CH_2$—, —O—C(O)—NH—$CH_2$—, —O—C(O)—NH—$CH_2$—$CH_2$, —, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—, —$CH_2$—$CH_2$—

$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, —$CH_2$—$CH_2$—$CH_2$—C(O)—NH—$CH_2$—$CH_2$—NH—C(O)—$CH_2$—$CH_2$—, —O—C(O)—NH—$[CH_2]_h$—$(OCH2CH2)_j$—, bivalent cycloalkyl group, —O—, —S—, an amino acid, —N($R^6$)—, and combinations of two or more of any of the foregoing, wherein $R^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—$(CH_2)_{1-6}$—NH—C(O)—, —NH—C(O)—NH—$(CH_2)_{1-6}$—NH—C(O)—, and —O—C(O)—NH—$(CH_2)_{1-6}$—NH—C(O)—, wherein the subscript values following each methylene indicate the number of methylenes contained in the structure, e.g., $(CH_2)_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —$(CH_2CH_2O)_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment. The spacer moiety does not include sugars or carbohydrates and it is preferred that the conjugate lacks substantially any water-soluble polymers attached directly, or through a spacer moiety, to a sugar or carbohydrate that, in turn, is attached to a Factor IX moiety.

In some instances, the conjugate may only have a single water-soluble polymer associated with a single Factor IX moiety. As a consequence, it may be desirous to have the water-soluble polymer be a non-linear water-soluble polymer (and prepare the conjugate using a non-linear polymeric reagent). A preferred non-linear water-soluble polymer is a branched water-soluble polymer, although multi-branched water-soluble polymers are included. By incorporating a branched water-soluble polymer, it is possible, for example, to double the effective molecular weight for each attachment site as compared to a single polymer.

Exemplary conjugates of the invention wherein the water-soluble polymer is in a branched form, include branched forms comprising a branched polymer and a branched approach comprising the structure:

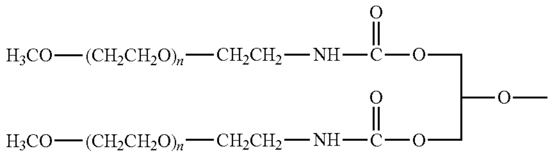

wherein each (n) is independently an integer having a value of from 2 to 3400.

Exemplary conjugates of the invention comprise the following structure:

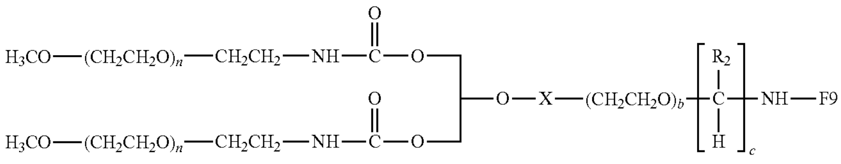

wherein:

each (n) is independently an integer having a value of from 2 to 3400;

X is spacer moiety;

(b) is an integer having a value 2 through 6;

(c) is an integer having a value 2 through 6;

$R^2$, in each occurrence, is independently H or lower alkyl; and

F9 is a Factor IX moiety.

An exemplary conjugate of the invention comprises the following structure:

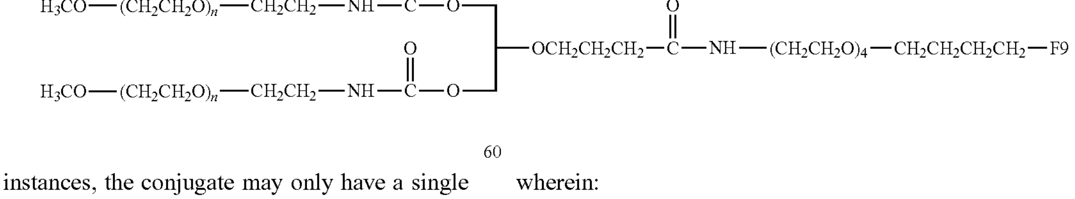

wherein:

each (n) is independently an integer having a value of from 2 to 3400; and

F9 is a Factor IX moiety.

Another exemplary conjugate of the invention comprises the following structure:

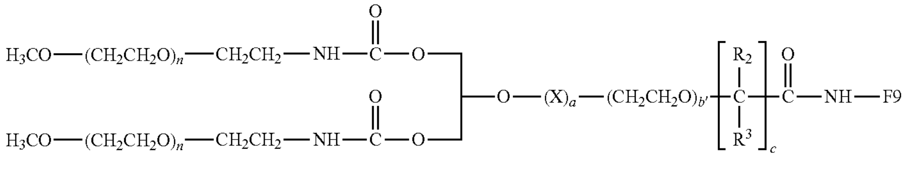

wherein:

each (n) is independently an integer having a value of from 2 to 3400;

(a) is either zero or one;

X, when present, is a spacer moiety comprised of one or more atoms;

(b') is zero or an integer having a value of one through ten;

(c) is an integer having a value of one through ten;

$R^2$, in each occurrence, is independently H or an organic radical;

$R^3$, in each occurrence, is independently H or an organic radical; and

F9 is a Factor IX moiety.)

An exemplary conjugates of the invention comprises the following structure:

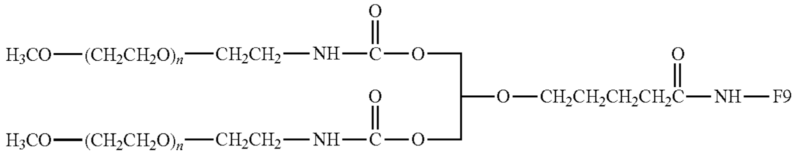

wherein:

each (n) is independently an integer having a value of from 2 to 3400; and

F9 is a Factor IX moiety.

Compositions

The conjugates are typically part of a composition. Generally, the composition comprises a plurality of conjugates, preferably although not necessarily, each having one, two, three or four water-soluble polymers separately covalently attached (either directly or through a spacer moiety) to one Factor IX moiety. The compositions, however, can also comprise other conjugates having four, five, six, seven, eight or more polymers attached to any given moiety having Factor IX activity. In addition, the invention includes instances wherein the composition comprises a plurality of conjugates, each conjugate comprising one water-soluble polymer covalently attached to one Factor IX moiety, as well as compositions comprising two, three, four, five, six, seven, eight, or more water-soluble polymers covalently attached to one Factor IX moiety.

In one or more embodiments of the invention, a composition is provided, the composition comprising a plurality of conjugates, wherein at least about 80% of all conjugates in the composition are each comprised of a Factor IX moiety covalently attached to one, two, three or four water-soluble polymers, and further wherein for each water-soluble polymer in the conjugate, the Factor IX moiety is attached to the water-soluble polymer either directly or through a spacer moiety comprised of one or more atoms.

With respect to the conjugates in the composition, the composition will typically satisfy one or more of the following characteristics: at least about 85% of the conjugates in the composition will have from one to five polymers attached to the Factor IX moiety; at least about 85% of the conjugates in the composition will have from one to four polymers attached to the Factor IX moiety; at least about 85% of the conjugates in the composition will have from one to three polymers attached to the Factor IX moiety; at least about 85% of the conjugates in the composition will have from one to two polymers attached to the Factor IX moiety; at least about 85% of the conjugates in the composition will have one polymer attached to the Factor IX moiety (i.e., be monoPEGylated); at least about 95% of the conjugates in the composition will have from one to five polymers attached to the Factor IX moiety; at least about 95% of the conjugates in the composition will have from one to four polymers attached to the Factor IX moiety; at least about 95% of the conjugates in the composition will have from one to three polymers attached to the Factor IX moiety; at least about 95% of the conjugates in the composition will have from one to two polymers attached to the Factor IX moiety; at least about 95% of the conjugates in the composition will have one polymer attached to the Factor IX moiety (i.e., be monoPEGylated); at least about 99% of the conjugates in the composition will have from one to five polymers attached to the Factor IX moiety; at least about 99% of the conjugates in the composition will have from one to four polymers attached to the Factor IX moiety; at least about 99% of the conjugates in the composition will have from one to three polymers attached to the Factor IX moiety; at least about 99% of the conjugates in the composition will have from one to two polymers attached to the Factor IX moiety; and at least about 99% of the conjugates in the composition will have one polymer attached to the Factor IX moiety (i.e., be monoPEGylated).

In one or more embodiments, it is preferred that the conjugate-containing composition is free or substantially free of albumin. It is also preferred that the composition is free or substantially free of proteins that do not have Factor IX activity. Thus, it is preferred that the composition is 85%, more preferably 95%, and most preferably 99% free of albumin. Additionally, it is preferred that the composition is 85%, more preferably 95%, and most preferably 99% free of any protein that does not have Factor IX activity. To the extent that albumin is present in the composition, exemplary compositions of the invention are substantially free of conjugates comprising a poly(ethylene glycol) polymer linking a residue of a Factor IX moiety to albumin.

Control of the desired number of polymers for any given moiety can be achieved by selecting the proper polymeric reagent, the ratio of polymeric reagent to the Factor IX moiety, temperature, pH conditions, and other aspects of the conjugation reaction. In addition, reduction or elimination of the undesired conjugates (e.g., those conjugates having four or more attached polymers) can be achieved through purification means.

For example, the polymer-Factor IX moiety conjugates can be purified to obtain/isolate different conjugated species. Specifically, the product mixture can be purified to obtain an average of anywhere from one, two, three, four, five or more PEGs per Factor IX moiety, typically one, two or three PEGs per Factor IX moiety. The strategy for purification of the final conjugate reaction mixture will depend upon a number of factors, including, for example, the molecular weight of the polymeric reagent employed, the particular Factor IX moiety, the desired dosing regimen, and the residual activity and in vivo properties of the individual conjugate(s).

If desired, conjugates having different molecular weights can be isolated using gel filtration chromatography and/or ion exchange chromatography. That is to say, gel filtration chromatography is used to fractionate differently numbered polymer-to-Factor IX moiety ratios (e.g., 1-mer, 2-mer, 3-mer, and so forth, wherein "1-mer" indicates 1 polymer attached to a Factor IX moiety, "2-mer" indicates two polymers attached to Factor IX moiety, and so on) on the basis of their differing molecular weights (where the difference corresponds essentially to the average molecular weight of the water-soluble polymer portion). For example, in an exemplary reaction where a 55,000 Dalton protein is randomly conjugated to a polymeric reagent having a molecular weight of about 20,000 Daltons, the resulting reaction mixture may contain unmodified protein (having a molecular weight of about 55,000 Daltons), monoPEGylated protein (or "1-mer") (having a molecular weight of about 75,000 Daltons), diPEGylated protein (or 2-mer" (having a molecular weight of about 95,000 Daltons), and so forth.

While this approach can be used to separate PEG and other polymer-Factor IX moiety conjugates having different molecular weights, this approach is generally ineffective for separating positional isomers having different polymer attachment sites within the Factor IX moiety. For example, gel filtration chromatography can be used to separate from each other mixtures of 1-mers, 2-mers, 3-mers, and so forth, although each of the recovered PEG-mer compositions may contain PEGs attached to different reactive amino groups (e.g., lysine residues) within Factor IX moiety.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) absorbance at 280 nm for protein content, (ii) dye-based protein analysis using bovine serum albumin as a standard, (iii) iodine testing for PEG content (Sims et al. (1980) *Anal. Biochem,* 107:60-63), (iv) sodium dodecyl sulfate polyacrylamide gel electrophoresis (SDS PAGE), followed by staining with barium iodide, and higher performance liquid chromatography.

Separation of positional isomers can be carried out by reverse phase chromatography using reverse phase-high performance liquid chromatography (RP-HPLC) methods using for example a C18 column or C3 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

The compositions are preferably substantially free of proteins that do not have Factor IX activity. In addition, the compositions preferably are substantially free of all other noncovalently attached water-soluble polymers. In some circumstances, however, the composition can contain a mixture of polymer-Factor IX moiety conjugates and unconjugated Factor IX.

Optionally, the composition of the invention further comprises a pharmaceutically acceptable excipient. If desired, the pharmaceutically acceptable excipient can be added to a conjugate to form a composition.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The amount of the conjugate (i.e., the conjugate formed between the active agent and the polymeric reagent) in the composition will vary depending on a number of factors, but will optimally be a therapeutically effective amount when the composition is stored in a unit dose container (e.g., a vial). In addition, the pharmaceutical preparation can be housed in a syringe. A therapeutically effective amount can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & (1995), the "Physician's Desk Reference", 52" ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

The compositions of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

The invention also provides a method for delivering a conjugate as provided herein to a patient suffering from a condition that is responsive to treatment with conjugate. The method comprises delivering, generally via injection, a therapeutically effective amount of the conjugate (preferably provided as part of a pharmaceutical composition). The conjugates (typically as part of a pharmaceutical composition) can be delivered by, for example, intravenous injection, intramuscular injection, subcutaneous injection, and so forth. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of delivering may be used to treat a patient having a condition that can be remedied or prevented by administration of the conjugate. Those of ordinary skill in the art appreciate which conditions a specific conjugate can effectively treat. For example, the conjugates can be used to treat individuals suffering from hemophilia B, either as a replacement therapy or on a prophylaxis basis. Administration of the conjugate for prophylaxis includes situations where a patient suffering from hemophilia B is about to undergo surgery and the conjugate is administered between one to four hours prior to surgery. In addition, the conjugates are suited for use as a prophylactic against uncontrolled bleeding, optionally in patients not suffering from hemophilia. Thus, for example, the conjugate can be administered to a patient at risk for uncontrolled bleeding prior to surgery.

The actual dose to be administered will vary depend upon the age, weight, and general condition of the subject as well as the severity of the condition being treated, the judgment of the health care professional, and conjugate being administered, Therapeutically effective amounts are known to those skilled in the art and/or are described in the pertinent reference texts and literature. Generally, on a weight basis, a therapeutically effective amount will range from about 0.001 mg to 100 mg, preferably in doses from 0.01 mg/day to 75 mg/day, and more preferably in doses from 0.10 mg/day to 50 mg/day. On an activity basis, corresponding doses based on international units of activity can be calculated by one of ordinary skill in the art.

The unit dosage of any given conjugate (again, preferably provided as part of a pharmaceutical composition) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis and the like, which are within the skill of the art. Such techniques are fully explained in the literature. Reagents and materials are commercially available unless specifically stated to the contrary. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level.

Although other abbreviations known by one having ordinary skill in the art will be referenced, other reagents and materials will be used, and other methods known by one having ordinary skill in the art will be used, the following list and methods description is provided for the sake of convenience.

NaCNBH$_3$ sodium cyanoborohydride, 95% (Aldrich)
HCl hydrochloric acid, glacial (Fisher)
K or kDa kilodaltons
Acetonitrile (Fisher Optima)
TFA Trifluoroacetic acid, HPLC grade (JT Baker)
PBS Phosphate buffered saline (Sigma)
SEC Size exclusion chromatography
HPLC high performance liquid chromatography
SDS-PAGE sodium dodecyl sulfate-polyacrylamide gel electrophoresis
HEPES [4-(2-hydroxyethyl)-1-piperazineethanesulfonic acid] biotechnology performance certified, 99.5+% (Sigma)
Ethyl alcohol, USP, Absolute-200 Proof (AAPER)
NuPAGE® MES [2-(N-morpholino)ethane sulfonic acid] SDS running buffer (Invitrogen Corporation, Carlsbad Calif.)
NuPAGE® 4×LDS (lithium dodecyl sulfate) sample buffer (Invitrogen Corporation, Carlsbad Calif.)
SigmaMarker, low range (M.W. 6,500-66,000) (Sigma)
SigmaMarker, high range (M.W. 36,000-205,000) (Sigma)
NuPAGE® Novex Bis-Tris [Bis(2-hydroxyethyl)imino-tris(hydroxymethyl)methane-HCl] gel (Invitrogen Corporation, Carlsbad Calif.)

SEC-HPLC Analysis

Size exclusion chromatography (SEC) was performed on an Agilent 1100 HPLC system (Agilent). For those samples analyzed using SEC-HPLC, each sample was analyzed using a SHODEX protein KW-804 column (Showa Denko KK, Tokyo Japan), at pH 7.2. The flow rate for the column was set at 0.5 mL/minute. Eluted protein and PEG-protein conjugates were detected using an UV-based approach having a wavelength set at 280 nm.

SDS-PAGE Analysis

Sodium dodecyl sulfate-polyacrylamide gel electrophoresis (SDS-PAGE) was performed using an XCELL SURE-LOCK Mini-Cell electrophoresis system (Invitrogen Corporation, Carlsbad Calif.). For those samples analyzed using SDS-PAGE, each sample was mixed with 4×LDS Sample Buffer (Invitrogen Corporation, Carlsbad Calif.). The prepared samples were then loaded onto a NuPAGE Novex 4-12% Bis-Tris gel and run for approximately thirty minutes at 200 V using NuPAGE® MES running buffer (Invitrogen Corporation, Carlsbad Calif.).

RP-HPLC Analysis

Reverse phase-high performance liquid chromatography was performed using a C3 reverse column (Hamilton, Zorbax). A 30-80% gradient of acetonitrile was used along with an elevated temperature over thirty minutes at 0.5 mL/minute.

Recombinant Factor IX corresponding to the amino acid sequence of SEQ. ID. NO. 1. was used in Examples 1-16. Factor IX was obtained in a buffer containing both L-histidine and glycine. Because the amine groups associated with L-histidine and glycine in the buffer would compete for amine groups associated with Factor IX, it was necessary to exchange the amine-containing buffer for an amine-free buffer to improve the Factor IX conjugation yield when amine-directed polymeric reagents were used to effect conjugation.

Briefly, the amine-containing buffer was exchanged for an amine-free buffer by one of two approaches, depending on the volume of buffer to be exchanged. For relatively small volumes of buffer, a 500 μL Zeba Desalt centrifuge column (Pierce Biotechnology, Rockford Ill.) was used according to the protocol provided by the manufacturer. For relatively large volumes of buffer, a 2 mL CENTRICON® centrifugal filter device (Millipore Corporation, Billerica Mass.) with a 10,000 or 30,000 Dalton molecular weight cutoff was used according to the protocol provided by the manufacturer. All samples used in the Examples without ethanol were changed to a 1×PBS buffer having a pH of 7.5, while all samples used in the Examples with ethanol were exchanged to a 1×PBS buffer having a pH of 7.5 with ethanol added to form a 10% ethanol-containing Factor IX reaction mixture.

The amine-free buffer containing recombinant Factor IX corresponding to the amino acid sequence of SEQ. ID. NO. 1. (the "Factor IX stock solution") was used in Examples 1-16. The Factor IX stock solution contained about 0.2 mg/mL to 0.55 mg/mL of Factor IX.

Example 1

PEGylation of Factor IX with mPEG-SMB, 30 kDa (1:1 Polymer to Factor IX Ratio; without Ethanol)

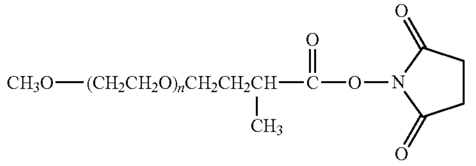

mPEG-SMB, 30kDa mPEG-SMB, 30 kDa, stored at −20° C. under argon, was warmed to ambient temperature. The warmed mPEG-SMB (4.1 mg) was dissolved in 1 mL of 2 mM HCl to form an mPEG-SMB solution. The mPEG-SMB solution was added to an aliquot of the Factor IX stock solution containing 0.07 mg of Factor IX until a one:one molar ratio of mPEG-SMB relative to Factor IX was reached. After the addition of the mPEG-SMB, the pH of the reaction was tested to ensure a pH of 7.2. to 7.5, and mixed well. To allow for coupling of the mPEG-SMB to Factor IX via an amide linkage, the reaction solution was stirred for three hours at room temperature, after which SDS PAGE was run on the sample, which confirmed the presence of monoconjugated material ("1-mer"). See the lane labeled as "1:1 30K SMB" in the gel provided as FIG. 1. Thereafter, coupling was allowed to continue by stirring the reaction solution for fifteen hours at 4° C., thereby resulting in a conjugate solution.

Figure 5:
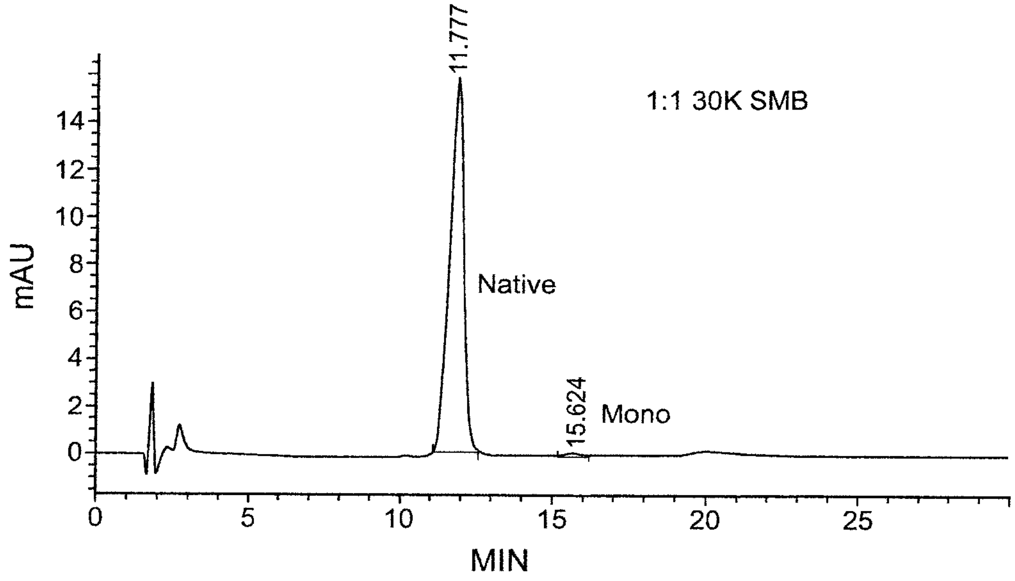
FIG. 5 is a plot corresponding to the resulting conjugation solution of Example 1.

RP-HPLC($C_3$) and a second SDS PAGE were used for the characterization of the resulting conjugate solution. Based on the second SDS PAGE result, conjugation was shown. See the lane labeled as "1:1 30K SMB" in the gel provided as FIG. 2. RP-HPLC($C_3$) was used to separate the components of the resulting conjugate solution and the resulting chromatogram indicated a yield of 0.54% (representing 100% monoPEGyled or "1-mer" species). See the chromatogram provided as FIG. 5.

It is expected that longer reactions times, increase temperatures and/or multiple additions of the polymeric reagent could increase yields. Using this same approach, other conjugates can be prepared using mPEG-SMB having other weight-average molecular weights.

Example 2

PEGylation of Factor IX with mPEG-SMB, 30 kDa (10:1 Polymer to Factor IX Ratio; without Ethanol)

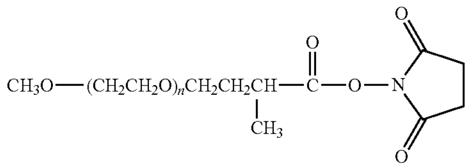

mPEG-SMB, 30kDa mPEG-SMB, 30 kDa, stored at −20° C. under argon, was warmed to ambient temperature. The warmed mPEG-SMB (4.1 mg) was dissolved in 1 mL of 2 mM to form an mPEG-SMB solution. The mPEG-SMB solution was added to an aliquot of the Factor IX stock solution containing 0.07 mg of Factor IX until a ten molar excess of mPEG-SMB relative to Factor IX was reached. After the addition of the mPEG-SMB, the pH of the reaction mixture was tested to ensure a pH of 7.2 to 7.5, and mixed well. To allow for coupling of the mPEG-SMB to Factor IX via an amide linkage, the reaction solution was stirred for three hours at room temperature, after which SDS PAGE was run on the sample, which confirmed the presence of monoconjugated material ("1-mer"). See the lane labeled as "10:1 30K SMB" in the gel provided as FIG. 1. Thereafter, coupling was allowed to continue by stirring the reaction solution for fifteen hours at 4° C., thereby resulting in a conjugate solution.

RP-HPLC($C_3$) and a second SDS PAGE were used for the characterization of the resulting conjugate solution. Based on the second SDS PAGE results, conjugation was shown.

Figure 2:
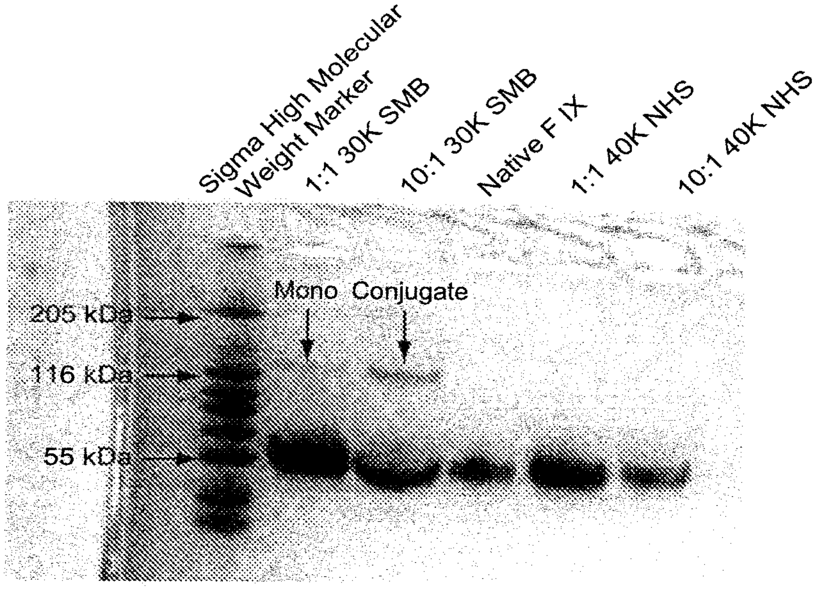
Figure 6:
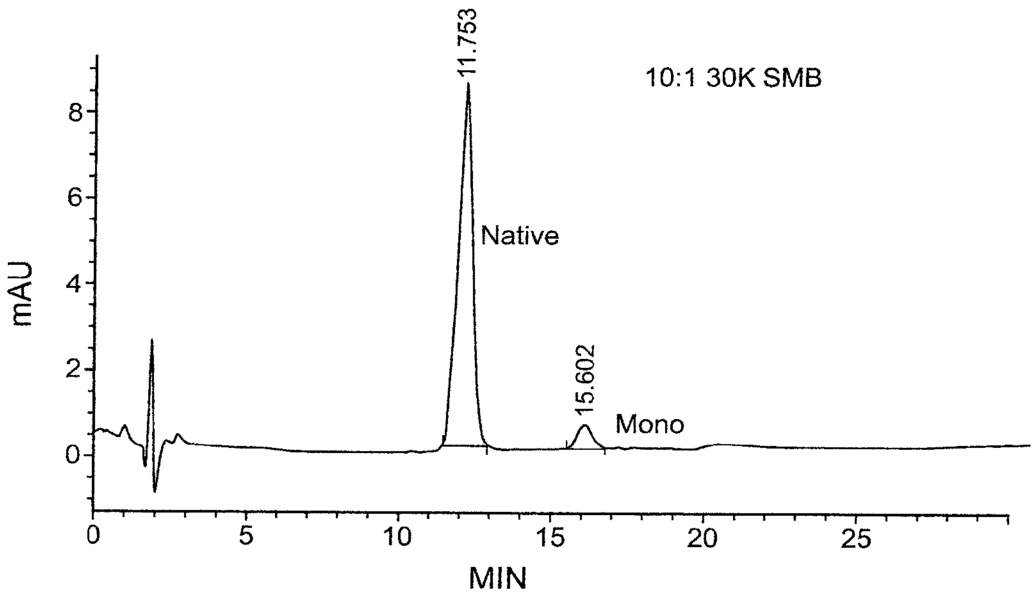
FIG. 6 is a plot corresponding to the resulting conjugation solution of Example 2.

See the lane labeled as "10:1 30K SMB" in the gel provided as FIG. 2. RP-HPLC($C_3$) was used to separate the components of the resulting conjugate solution and the resulting chromatogram indicated a yield of 6.4% (representing 100% monoPEGyled or "1-mer" species). See the chromatogram provided as FIG. 6.

Figure 4:
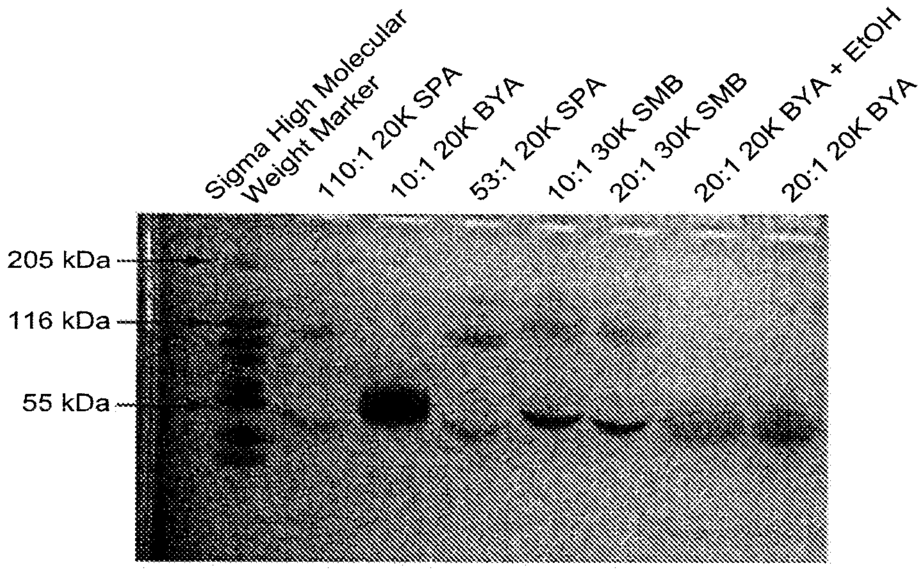
FIG. 4 is a copy of a gel resulting from SDS-PAGE analysis of samples described in Examples 2, 9 and 12 through 16.

It is expected that longer reactions times, increased temperatures and/or multiple additions of the polymeric reagent could increase yields. Thus, when this experiment was repeated for an extended time at room temperature prior to continuing the reaction overnight at 4° C., an increase conjugate yield resulted as evidenced by a darker band as seen in an SDS PAGE gel. See the lane labeled as "10:1 30K SMB" in FIG. 4. Using the same approaches described here, other conjugates can be prepared using mPEG-SMB having other weight-average molecular weights.

Example 3

PEGylation of Factor IX with Branched mPEG2-N-Hydroxysuccinimide, 40 kDa (1:1 Polymer to Factor IX Ratio; without Ethanol)

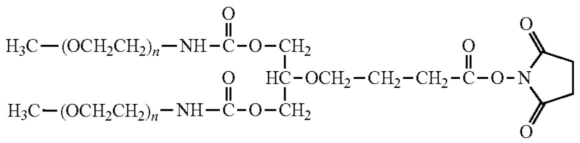

Branched mPEG2-N-Hydroxysuccinimide, 40kDa

Branched mPEG2-N-hydroxysuccinimide, 40 kDa, stored at −20° C. under argon, was warmed to ambient temperature. The warmed branched mPEG2-N-hydroxysuccinimide (2.0 mg) was dissolved in 1 mL of 2 mM HCl to form a branched mPEG2-N-hydroxysuccinimide solution. The branched mPEG2-N-hydroxysuccinimide solution was added to an aliquot of the Factor IX stock solution containing 0.07 mg of Factor IX until a one:one molar ratio of branched mPEG2-N-hydroxysuccinimide relative to Factor IX was reached. After the addition of branched mPEG2-N-hydroxysuccinimide, the pH of the reaction mixture was tested to ensure a pH of 7.2 to 7.5, and mixed well. To allow for coupling of the branched mPEG2-N-hydroxysuccinimide to Factor IX via an amide linkage, the reaction solution was stirred for three hours at room temperature, after which SDS PAGE was run on the sample, which showed no detectable conjugation. See the lane labeled as "1:1 40K NHS" in the gel provided as FIG. 1. Thereafter, addition time for conjugation was provided by stirring the reaction solution for fifteen hours at 4° C., thereby resulting in a conjugate solution.

Figure 7:
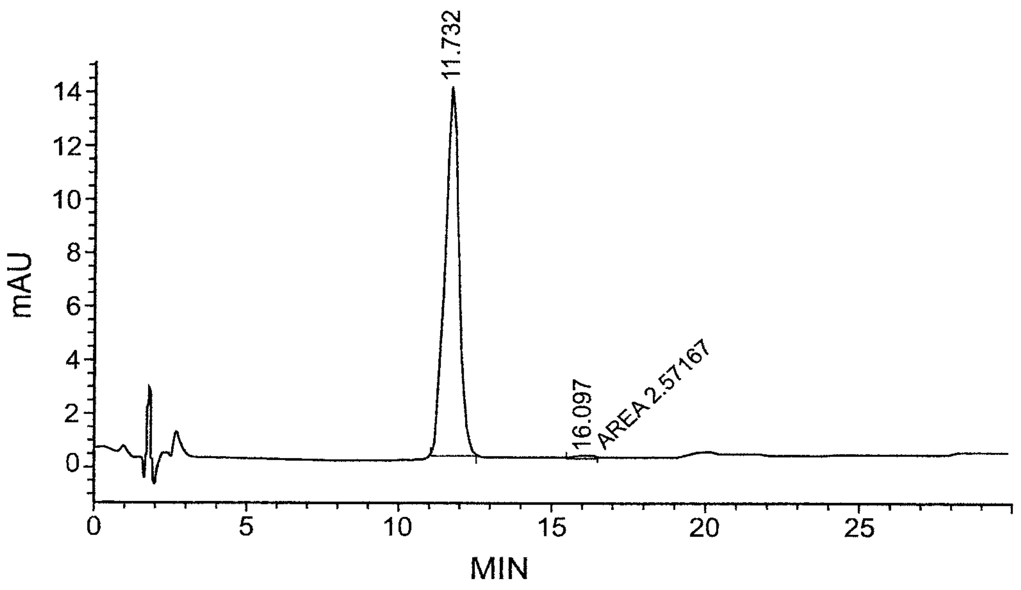
FIG. 7 is a plot corresponding to the resulting conjugation solution of Example 3.

RP-HPLC($C_3$) and a second SDS PAGE were used for the characterization of the resulting conjugate solution. Based on the second SDS PAGE results, conjugation was shown. See the lane labeled as "1:1 40K NHS" in the gel provided as FIG. 2. RP-HPLC($C_3$) was used to separate the components of the resulting conjugate solution and the resulting chromatogram indicated a yield of 0.1% (representing 100% monoPEGyled or "1-mer" species). See the chromatogram provided as FIG. 7.

It is expected that longer reactions times, increased temperatures and/or multiple additions of the polymeric reagent could increase yields. Using this same approach, other conjugates can be prepared using branched mPEG2-N-hydroxysuccinimide having other weight-average molecular weights.

Example 4

PEGylation of Factor IX with Branched mPEG2-N-Hydroxysuccinimide, 40 kDa (10:1 Polymer to Factor IX Ratio; without Ethanol)

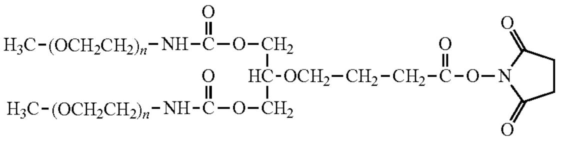

Branched mPEG2-N-Hydroxysuccinimide, 40kDa

Branched mPEG2-N-hydroxysuccinimide, 40 kDa, stored at −20° C. under argon, was warmed to ambient temperature. The warmed branched mPEG2-N-hydroxysuccinimide (2.0 mg) was dissolved in 1 mL of 2 mM HCl to form a branched mPEG2-N-hydroxysuccinimide solution. The branched mPEG2-N-hydroxysuccinimide solution was added to an aliquot of the Factor IX stock solution containing 0.07 mg of Factor IX until a ten molar excess of branched mPEG2-N-hydroxysuccinimide relative to Factor IX was reached. After the addition of branched mPEG2-N-hydroxysuccinimide, the pH of the reaction mixture was tested to ensure a pH of 7.2 to 7.5, and mixed well. To allow for coupling of the branched mPEG2-N-hydroxysuccinimide to Factor IX via an amide linkage, the reaction solution was stirred for three hours at room temperature, after which SDS PAGE was run on the sample, which showed no detectable conjugation. See the lane labeled as 10:1 40 k NHS" in the gel provided as FIG. 1. Thereafter, coupling was allowed to continue by stirring the reaction solution for fifteen hours at 4° C., thereby resulting in a conjugate solution.

Figure 8:
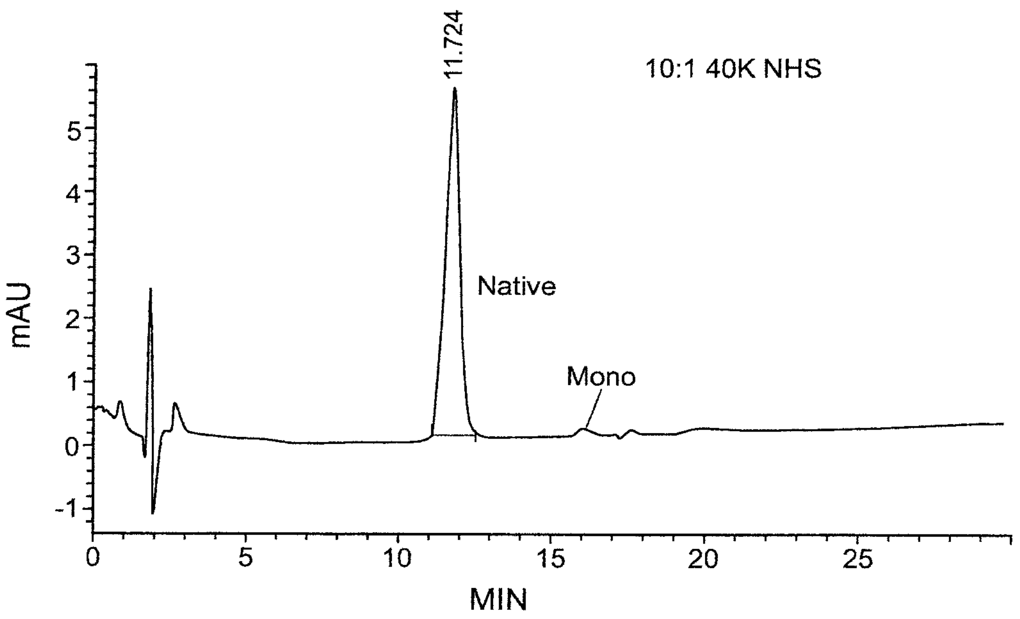
FIG. 8 is a plot corresponding to the resulting conjugation solution of Example 4

RP-HPLC($C_3$) and a second SDS PAGE were used for the characterization of the resulting conjugate solution. Based on the second SDS PAGE results, conjugation was still not detectable. See the lane labeled as "10:1 40K NHS" in the gel provided as FIG. 2. RP-HPLC($C_3$) was used to separate the components of the resulting conjugate solution and the resulting chromatogram indicated no detectable conjugate yield. See the chromatogram provided as FIG. 8.

It is expected that longer reactions times, increased temperatures and/or multiple additions of the polymeric reagent could increase yields, Using this same approach, other conjugates can be prepared using branched mPEG2-N-hydroxysuccinimide having other weight-average molecular weights.

Example 5

PEGylation of Factor IX with mPEG-SMB, 30 kDa (10:1 Polymer to Factor IX Ratio; with Ethanol)

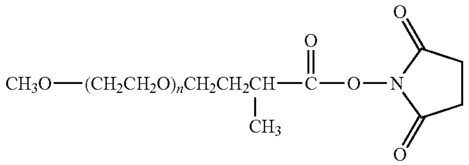

mPEG-SMB, 30kDa

As ethanol is believed to increase the structural flexibility of certain proteins, ethanol was introduced into the buffer and reaction system. mPEG-SMB, 30 kDa, stored at −20° C. under argon, was warmed to ambient temperature. The warmed mPEG-SMB (10.0 mg) was dissolved in 0.5 mL of 2 mM HCl with ethanol added to form a 10% ethanol-containing mPEG-SMB solution. The 10% ethanol-containing mPEG-SMB solution was added to the 10% ethanol-containing Factor IX reaction mixture until a ten molar excess of mPEG-SMB relative to Factor IX was reached. After the addition of the mPEG-SMB, the pH of the reaction mixture was tested to ensure a pH of 7.2 to 7.5, and mixed well. To allow for coupling of the mPEG-SMB to Factor IX via an amide linkage, the reaction solution was stirred for three hours at room temperature. Coupling was allowed to continue by stirring the reaction solution overnight at 4° C., thereby resulting in a conjugate solution.

Figure 3:
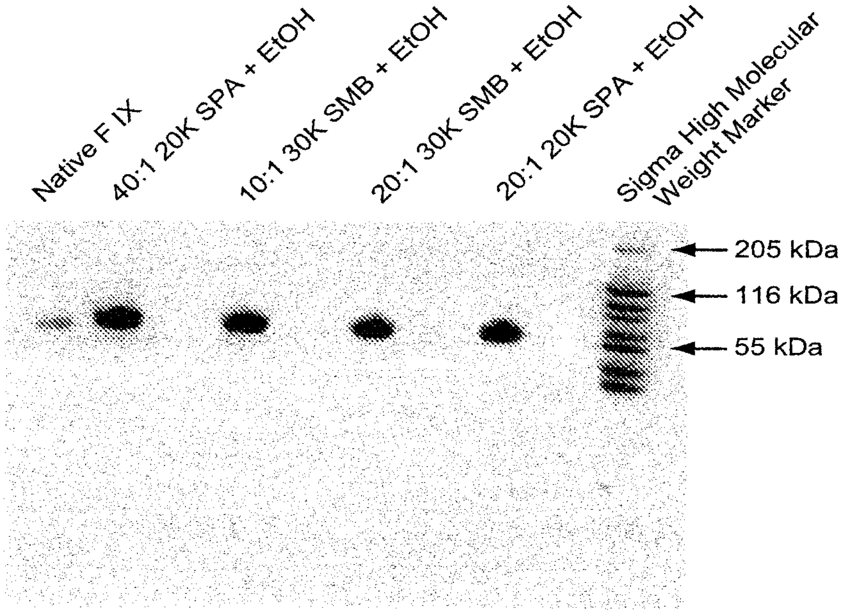
FIG. 3 is a copy of a gel resulting from SDS-PAGE analysis of samples described in Examples 5, 6, 10 and 11.

SDS PAGE was used for the characterization of the resulting conjugate solution. Based on the SDS PAGE results, conjugation was not detected. See the lane labeled as "10:1 30K SMB+EtOH" in the gel provided as FIG. 3. It is now believed that the introduction of ethanol does not increase the structural flexibility of Factor IX to allow for increased conjugation of mPEG-SMB, 30 kDa.

It is expected that longer reactions times, increased temperatures and/or multiple additions of the polymeric reagent could increase yields. Using this same approach, other conjugates can be prepared using mPEG-SMB having other weight-average molecular weights.

Example 6

PEGylation of Factor IX with mPEG-SMB, 30 kDa (20:1 Polymer to Factor IX Ratio; with Ethanol)

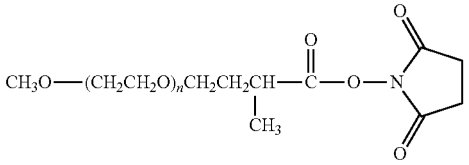

mPEG-SMB, 30kDa

As ethanol is believed to increase the structural flexibility of certain proteins, ethanol was introduced into the buffer and reaction system, mPEG-SMB, 30 kDa, stored at −20° C. under argon, was warmed to ambient temperature. The warmed mPEG-SMB (10.0 mg) was dissolved in 0.5 mL of 2 mM HCl with ethanol added to form a 10% ethanol-containing mPEG-SMB solution. The 10% ethanol-containing mPEG-SMB solution was added to the 10% ethanol-containing Factor IX reaction mixture until a twenty molar excess of mPEG-SMB relative to Factor IX was reached. After the addition of the mPEG-SMB, the pH of the reaction mixture was tested to ensure a pH of 7.2 to 7.5, and mixed well. To allow for coupling of the mPEG-SMB to Factor IX via an amide linkage, the reaction solution was stirred for three hours at room temperature. Coupling was allowed to continue by stirring the reaction solution overnight at 4° C., thereby resulting in a conjugate solution.

SDS PAGE was used for the characterization of the resulting conjugate solution. Based on the SDS PAGE results, conjugation was not detected. See the lane labeled as "20:1 30K SMB+EtOH" in the gel provided as FIG. 3. It is now believed that the introduction of ethanol does not increase the structural flexibility of Factor IX to allow for increased conjugation of mPEG-SMB, 30 kDa.

It is expected that longer reactions times, increased temperatures and/or multiple additions of the polymeric reagent could increase yields. Using this same approach, other conjugates can be prepared using mPEG-SMB having other weight-average molecular weights.

Example 7

PEGylation of Factor IX with Branched mPEG2-N-Hydroxysuccinimide, 40 kDa (10:1 Polymer to Factor IX Ratio; with Ethanol)

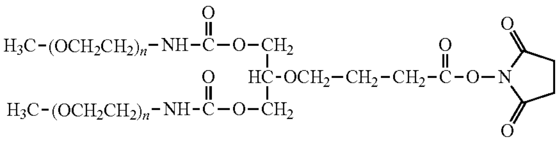

Branched mPEG2-N-Hydroxysuccinimide, 40kDa

As ethanol is believed to increase the structural flexibility of certain proteins, ethanol was introduced into the buffer and reaction system. Branched mPEG2-N-hydroxysuccinimide, 40 kDa, stored at −20° C. under argon, was warmed to ambient temperature. The warmed branched mPEG2-N-hydroxysuccinimide (2.0 mg) was dissolved in 1.0 mL of 2 mM HCl with ethanol added to form a 10% ethanol-containing branched mPEG2-N-hydroxysuccinimide solution. The 10% ethanol-containing branched mPEG2-N-hydroxysuccinimide solution was added to the 10% ethanol-containing Factor IX reaction mixture until a ten molar excess of branched mPEG2-N-hydroxysuccinimide relative to Factor IX was reached. After the addition of branched mPEG2-N-hydroxysuccinimide, the pH of the reaction mixture was tested to ensure a pH of 7.2 to 7.5, and mixed well. To allow for coupling of the branched mPEG2-N-hydroxysuccinimide to Factor IX via an amide linkage, the reaction solution was stirred for three hours at room temperature. Coupling was allowed to continue by stirring the reaction solution overnight at 4° C., thereby resulting in a conjugate solution.

SDS PAGE was used for the characterization of the resulting conjugate solution. Based on the SDS PAGE results, conjugation was not detected (results not shown), It is now believed that the introduction of ethanol does not increase the structural flexibility of Factor IX to allow for increased conjugation of branched mPEG2-N-hydroxysuccinimide, 40 kDa.

It is expected that longer reactions times, increased temperatures and/or multiple additions of the polymeric reagent could increase yields. Using this same approach, other conjugates can be prepared using branched mPEG2-N-hydroxysuccinimide having other weight-average molecular weights.

Example 8

PEGylation of Factor IX with Branched mPEG2-N-Hydroxysuccinimide, 40 kDa (20:1 Polymer to Factor IX Ratio; with Ethanol)

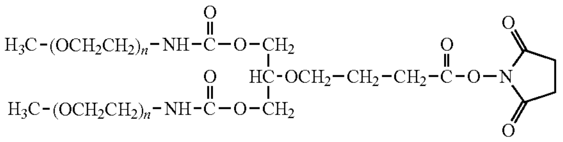

Branched mPEG2-N-Hydroxysuccinimide, 40kDa

As ethanol is believed to increase the structural flexibility of certain proteins, ethanol was introduced into the buffer and reaction system, Branched mPEG2-N-hydroxysuccinimide, 40 kDa, stored at −20° C. under argon, was warmed to ambient temperature. The warmed branched mPEG2-N-hydroxysuccinimide (2.0 mg) was dissolved in 1.0 mL of 2 mM HCl with ethanol added to form a 10% ethanol-containing branched mPEG2-N-hydroxysuccinimide solution. The 10% ethanol-containing branched mPEG2-N-hydroxysuccinimide solution was added to the 10% ethanol-containing Factor IX reaction mixture until a twenty molar excess of branched mPEG2-N-hydroxysuccinimide relative to Factor IX was reached. After the addition of branched mPEG2-N-hydroxysuccinimide, the pH of the reaction mixture was tested to ensure a pH of 7.2 to 7.5, and mixed well. To allow for coupling of the branched mPEG2-N-hydroxysuccinimide to Factor IX via an amide linkage, the reaction solution was stirred for three hours at room temperature. Coupling was allowed to continue by stirring the reaction solution overnight at 4° C., thereby resulting in a conjugate solution.

SDS PAGE was used for the characterization of the resulting conjugate solution. Based on the SDS PAGE results, conjugation was not detected (results not shown). It is now believed that the introduction of ethanol does not increase the structural flexibility of Factor IX to allow for increased conjugation of branched mPEG2-N-hydroxysuccinimide, 40 kDa.

It is expected that longer reactions times, increased temperatures and/or multiple additions of the polymeric reagent could increase yields. Using this same approach, other conjugates can be prepared using branched mPEG2-N-hydroxysuccinimide having other weight-average molecular weights.

Example 9

PEGylation of Factor IX with mPEG-SMB, 30 kDa (20:1 Polymer to Factor IX Ratio; without Ethanol)

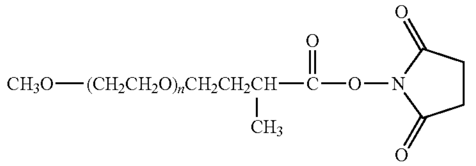

mPEG-SMB, 30kDa mPEG-SMB, 30 kDa, stored at −20° C. under argon, was warmed to ambient temperature. The warmed mPEG-SMB (8.6 mg) was dissolved in 1.0 mL of 2 mM HCl to form an mPEG-SMB solution. The mPEG-SMB solution was added to an aliquot of the Factor IX stock solution containing 0.07 mg of Factor IX until a twenty molar excess of mPEG-SMB relative to Factor IX was reached. After the addition of the mPEG-SMB, the pH of the reaction mixture was tested to ensure a pH of 7.2 to 7.5. To allow for coupling of the mPEG-SMB to Factor IX via an amide linkage, the reaction solution was stirred for two hours at room temperature. Coupling was allowed to continue by stirring the reaction solution overnight at 4° C., thereby resulting in a conjugate solution. Thereafter, coupling was allowed to continue by stirring overnight at 4° C., thereby resulting in a conjugate solution.

SDS PAGE was used for the characterization. Based on the second SDS PAGE results, conjugation was shown. See the lane labeled as "20:1 30K SMB" in the gel provided as FIG. 4.

It is expected that longer reactions times, increased temperatures and/or multiple additions of the polymeric reagent could increase yields. Using this same approach, other conjugates can be prepared using branched mPEG-SMB having other weight-average molecular weights.

Example 10

PEGylation of Factor IX with mPEG-SPA, 20 kDa (20:1 Polymer to Factor IX Ratio; with Ethanol)

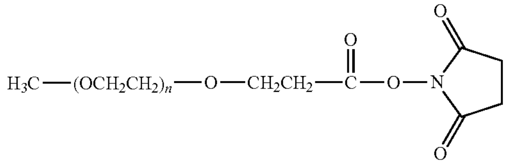

mPEG-SPA, 20kDa

As ethanol is believed to increase the structural flexibility of certain proteins, ethanol was introduced into the buffer and reaction system. mPEG-SPA, 20 kDa, stored at −20° C. under argon, was warmed to ambient temperature. The warmed mPEG-SPA (10.0 mg) was dissolved in 0.5 mL of 2 mM HCl with ethanol added to form a 10% ethanol-containing mPEG- SPA solution. The 10% ethanol-containing mPEG-SPA solution was added to the 10% ethanol-containing Factor IX reaction mixture until a twenty molar excess of mPEG-SPA relative to Factor IX was reached. After the addition of the mPEG-SPA, the pH of the reaction mixture was tested to ensure a pH of 7.2 to 7.5, and mixed well. To allow for coupling of the mPEG-SPA to Factor IX via an amide linkage, the reaction solution was stirred for two hours at room temperature. Coupling was allowed to continue by stirring the reaction solution.

Based on SDS PAGE results, conjugation was not detected. See the lane labeled as "20:1 20K SPA+EtOH" in the gel provided as FIG. 3. It is now believed that the introduction of ethanol does not increase the structural flexibility of Factor IX to allow for increased conjugation of mPEG-SPA, 20 kDa.

It is expected that longer reactions times, increased temperatures and/or multiple additions of the polymeric reagent could increase yields. Using this same approach, other conjugates can be prepared using mPEG-SPA having other weight-average molecular weights.

Example 11

PEGylation of Factor IX with mPEG-SPA, 20 kDa (40:1 Polymer to Factor IX Ratio; with Ethanol)

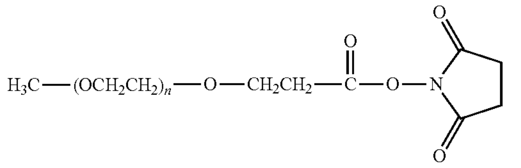

mPEG-SPA, 20kDa

As ethanol is believed to increase the structural flexibility of certain proteins, ethanol was introduced into the buffer and reaction system. mPEG-SPA, 20 kDa, stored at −20° C. under argon, was warmed to ambient temperature. The warmed mPEG-SPA (10.0 mg) was dissolved in 0.5 mL of 2 mM HCl with ethanol added to form a 10% ethanol-containing mPEG-SPA solution. The 10% ethanol-containing mPEG-SPA solution was added to the 10% ethanol-containing Factor IX reaction mixture until a forty molar excess of mPEG-SPA relative to Factor IX was reached. After the addition of the mPEG-SPA, the pH of the reaction mixture was tested to ensure a pH of 7.2 to 7.5, and mixed well. To allow for coupling of the mPEG-SPA to Factor IX via an amide linkage, the reaction solution was stirred for two hours at room temperature. Coupling was allowed to continue by stirring the reaction solution.

Based on SDS PAGE results, conjugation was not detected. See the lane labeled as "40:1 20K SPA+EtOH" in the gel provided as FIG. 3. It is now believed that the introduction of ethanol does not increase the structural flexibility of Factor IX to allow for increased conjugation of mPEG-SPA, 20 kDa.

It is expected that longer reactions times, increased temperatures and/or multiple additions of the polymeric reagent could increase yields. Using this same approach, other conjugates can be prepared using mPEG-SPA having other weight-average molecular weights.

Example 12

PEGylation of Factor IX with Branched mPEG-Butyraldehyde, 20 kDa (10:1 Polymer to Factor IX Ratio; without Ethanol)

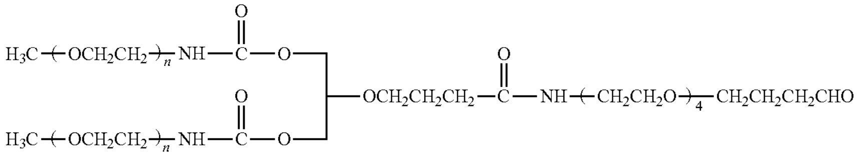

Branched mPEG2-Butyraldehyde, 20kDa

Branched mPEG2-Butyraldehyde, 20 kDa, stored at −20° C. under argon, was warmed to ambient temperature. The warmed branched mPEG2-butyraldehyde (10.9 mg) was dissolved in 1 mL of 2 mM HCl to form a branched mPEG2-butyraldehyde solution. The branched mPEG2-butyraldehyde solution was added to an aliquot of the Factor IX stock solution containing 0.07 mg of Factor IX until a ten molar excess of branched mPEG2-butyraldehyde to Factor IX was reached. After thirty minutes of mixing, a reducing agent, $NaCNBH_3$ (dissolved in 1×PBS), was added at excess relative to the branched mPEG2-butyraldehyde (with the pH tested and adjusted as necessary to ensure reduction to the secondary amine). The solution was then stirred overnight at 4° C. to ensure coupling via an amine linkage.

Figure 9:
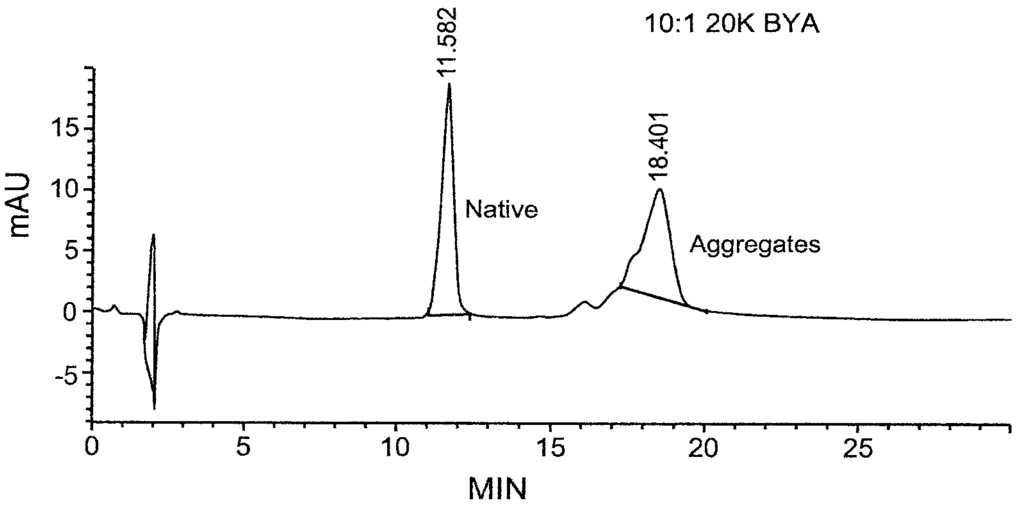
FIG. 9 is a plot corresponding to the resulting conjugation solution of Example 12.

RP-HPLC($C_3$) and a SDS PAGE were used for the characterization of the resulting conjugate solution. Based on the SDS PAGE results, conjugation was not detected. See the lane labeled as "10:1 20K BYA" in the gel provided as FIG. 4. RP-HPLC($C_3$) was used to separate the components of the resulting conjugate solution and the resulting chromatogram did not confirm the presence of conjugated material. See the chromatogram provided as FIG. 9.

It is expected that longer reactions times, increased temperatures and/or multiple additions of the polymeric reagent could increase yields. Using this same approach, other conjugates can be prepared using branched mPEG2-butyraldehyde having other weight-average molecular weights.

Example 13

PEGylation of Factor IX with Branched mPEG-Butyraldehyde, 20 kDa (20:1 Polymer to Factor IX Ratio; without Ethanol)

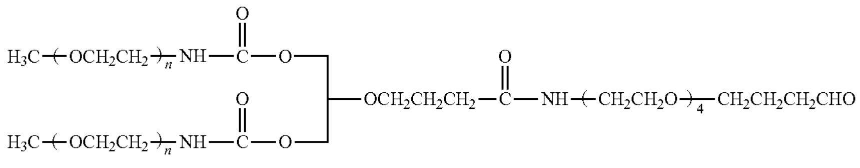

Branched mPEG2-Butyraldehyde, 20kDa

Branched mPEG2-Butyraldehyde, 20 kDa, stored at −20° C. under argon, was warmed to ambient temperature. The warmed branched mPEG2-butyraldehyde (10.9 mg) was dissolved in 1 mL of 2 mM HCl to form a branched mPEG2-butyraldehyde solution. The branched mPEG2-butyraldehyde solution was added to an aliquot of the Factor IX stock solution containing 0.07 mg of Factor IX until a twenty molar excess of branched mPEG2-butyraldehyde to Factor IX was reached. After thirty minutes of mixing, a reducing agent, $NaCNBH_3$ (dissolved in 1×PBS), was added at excess relative to the branched mPEG2-butyraldehyde (with the pH tested and adjusted as necessary to ensure reduction to the secondary amine). The solution was then stirred overnight at 4° C. to ensure coupling via an amine linkage.

Figure 10:
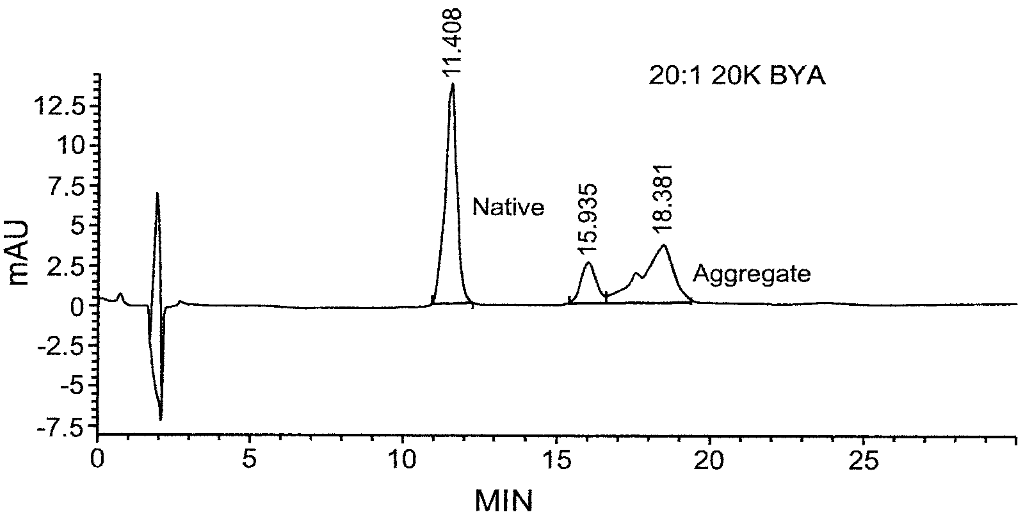
FIG. 10 is a plot corresponding to the resulting conjugation solution of Example 13.

RP-HPLC($C_3$) and a SDS PAGE were used for the characterization of the resulting conjugate solution. Based on the SDS PAGE results, conjugation was not detected. See the lane labeled as "20:1 20K BYA" in the gel provided as FIG. 4. RP-HPLC($C_3$) was used to separate the components of the resulting conjugate solution and the resulting chromatogram did not confirm the presence of conjugated material. See the chromatogram provided as FIG. 10.

It is expected that longer reactions times, increased temperatures and/or multiple additions of the polymeric reagent could increase yields. Using this same approach, other conjugates can be prepared using branched mPEG2-butyraldehyde having other weight-average molecular weights.

Example 14

PEGylation of Factor IX with mPEG-SPA, 20 kDa (53:1 Polymer to Factor IX Ratio; without Ethanol)

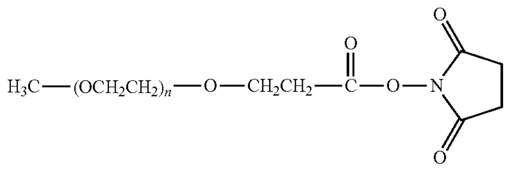

mPEG-SPA, 20kDa mPEG-SPA, 20 kDa, stored at −20° C. under argon, was warmed to ambient temperature. The warmed mPEG-SPA (5.4 mg) was dissolved in 1 mL of 2 mM HCl to form an mPEG-SPA solution. The mPEG-SPA solution was added to an aliquot of the Factor IX stock solution containing 0.07 mg of Factor IX until a fifty-three molar excess of mPEG-SPA relative to Factor IX was reached. After the addition of the mPEG-SPA, the pH of the reaction mixture was tested to ensure a pH of 7.2 to 7.5. To allow for coupling of the mPEG-SPA to Factor IX via an amide linkage, the reaction solution was stirred for two hours at room temperature. Coupling was allowed to continue by stirring the reaction solution overnight at 4° C., thereby resulting in a conjugate solution.

Figure 11:
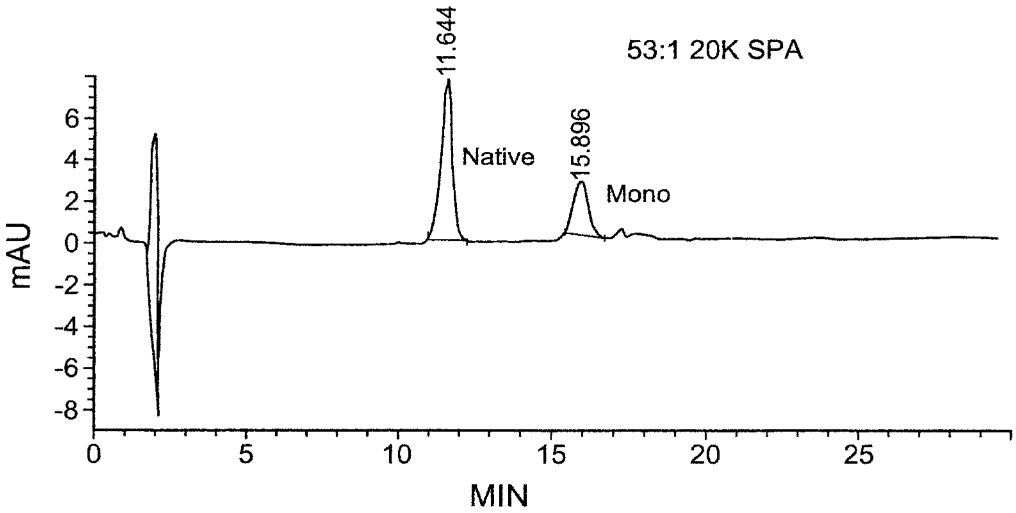
FIG. 11 is a plot corresponding to the resulting conjugation solution of Example 14.

RP-HPLC($C_3$) and a second SDS PAGE were used for the characterization of the resulting conjugate solution. Based on the SDS PAGE results, conjugation was verified. See the lane labeled "53:1 20K SPA" in the gel provided as FIG. 4. RP-HPLC($C_3$) was used to separate the components of the resulting conjugate solution and the resulting chromatogram indicated approximately 60% conjugation yield (comprising 51.9% monoPEGylated or "1-mer" species and 8% diPEGylated or "2-mer" species). See the chromatogram provided as FIG. 11, It is believed, however, that the actual yield may be somewhat lower due to the relatively large excess of polymeric reagent.

Using this same approach, other conjugates can be prepared using mPEG-SPA having other weight-average molecular weights.

Example 15

PEGylation of Factor IX with mPEG-SPA, 20 kDa (110:1 Polymer to Factor IX Ratio; without Ethanol)

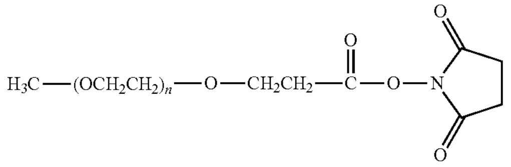

mPEG-SPA, 20kDa mPEG-SPA, 20 kDa, stored at −20° C. under argon, was warmed to ambient temperature. The warmed mPEG-SPA (5.4 mg) was dissolved in 1 mL of 2 mM HCl to form an mPEG-SPA solution. The mPEG-SPA solution was added to an aliquot of the Factor IX stock solution containing 0.07 mg of Factor IX until a one hundred-ten molar excess of mPEG-SPA relative to Factor IX was reached. After the addition of the mPEG-SPA, the pH of the reaction mixture was tested to ensure a pH of 7.2 to 7.5. To allow for coupling of the mPEG-SPA to Factor IX via an amide linkage, the reaction solution was stirred for two hours at room temperature. Coupling was allowed to continue by stirring the reaction solution overnight at 4° C., thereby resulting in a conjugate solution.

Figure 12:
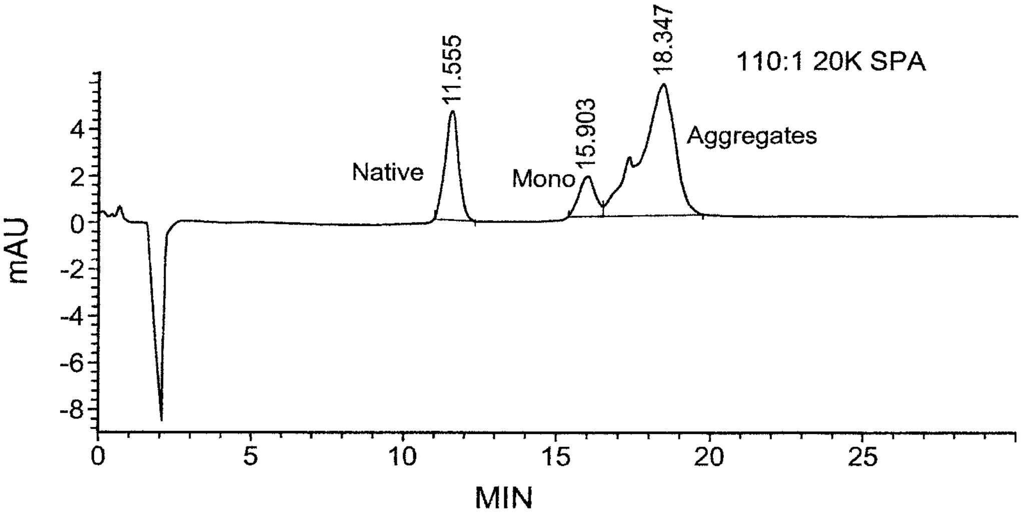
FIG. 12 is a plot corresponding to the resulting conjugation solution of Example 15.
Figure 13:
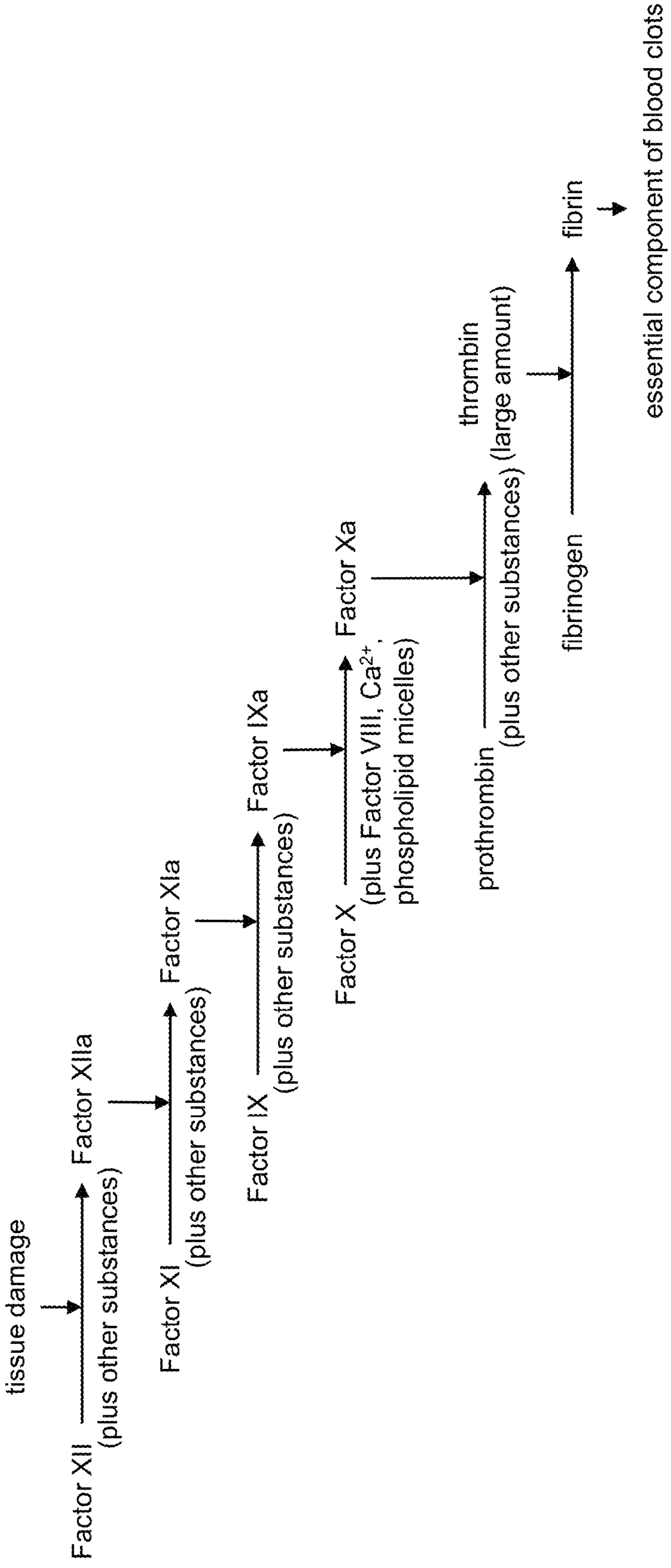
FIG. 13 demonstrates the role of Factor IX in the intrinsic pathway of blood clotting.

RP-HPLC($C_3$) and a second SDS PAGE were used for the characterization of the resulting conjugate solution. Based on the SDS PAGE results, conjugation was verified. See the lane labeled "110:1 20K SPA" in the gel provided as FIG. 4. RP-HPLC($C_3$) was used to separate the components of the resulting conjugate solution and the resulting chromatogram indicated approximately 44% conjugation yield (representing approximately 100% monoPEGylated or "1-mer" species). See the chromatogram provided as FIG. 12. It is believed, however, that the actual yield may be somewhat lower due to the relatively large excess of polymeric reagent.

Using this same approach, other conjugates can be prepared using mPEG-SPA having other weight-average molecular weights.

Example 16

PEGylation of Factor IX with Branched mPEG-Butyraldehyde, 20 kDa (20:1 Polymer to Factor IX Ratio; with Ethanol)

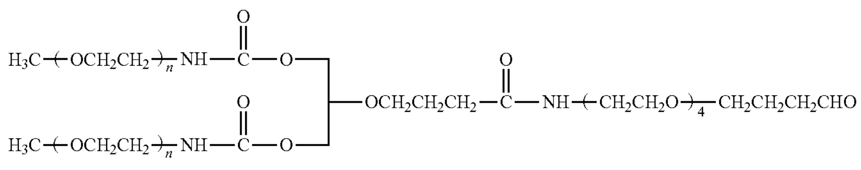

Branched mPEG2-Butyraldehyde, 20kDa

As ethanol is believed to increase the structural flexibility of certain proteins, ethanol was introduced into the buffer and reaction system. Branched mPEG2-Butyraldehyde, 20 kDa, stored at −20° C. under argon, was warmed to ambient temperature. The warmed branched mPEG2-butyraldehyde (10.9 mg) was dissolved in 1 mL of 2 mM HCl with ethanol added to form a 10% ethanol-containing branched mPEG2-butyraldehyde solution. The 10% ethanol-containing branched mPEG2-butyraldehyde solution was added to an aliquot of the Factor IX stock solution containing 0.07 mg of Factor IX until a twenty molar excess of branched mPEG2-butyraldehyde to Factor IX was reached. After thirty minutes of mixing, a reducing agent, $NaCNBH_3$ (dissolved in 1×PBS), was added at excess relative to the branched mPEG2-butyraldehyde (with the pH tested and adjusted as necessary to ensure reduction to the secondary amine). The solution was then stirred overnight at 4° C. to ensure coupling via an amine linkage.

RP-HPLC($C_3$) and a SDS PAGE were used for the characterization of the resulting conjugate solution. Based on the SDS PAGE results, conjugation was not detected. See the lane labeled as "20:1 20K BYA+EtOH" in the gel provided as FIG. 4. RP-HPLC($C_3$) confirmed the absence of detectable conjugated material (results not shown). It is now believed that the introduction of ethanol does not increase the structural flexibility of Factor IX to allow for increased conjugation of branched mPEG2-butyraldehyde.

It is expected that longer reactions times, increased temperatures and/or multiple additions of the polymeric reagent could increase yields. Using this same approach, other conjugates can be prepared using branched mPEG2-butyraldehyde having other weight-average molecular weights.

Example 17

PEGylation of Factor IXa with mPEG-SBA mPEG-Succinimidyl butanoate having a molecular weight of 10,000 Daltons is obtained from Nektar Therapeutics, (Huntsville, Ala.). The basic structure of the polymer reagent is provided below:

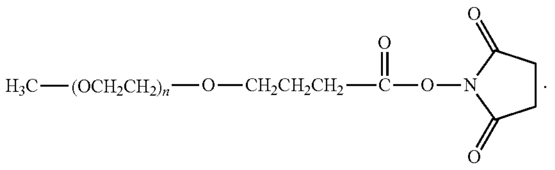

If lyophilized, Factor IXa is dissolved in amine-free buffer such as phosphate to result in a final pH to 7.2-9. To this solution is then added a 1.5 to 10-fold molar excess of mPEG-SBA. The resulting mixture is stirred at room temperature for several hours.

The reaction mixture is analyzed by SDS-PAGE to determine the degree of PEGylation of the protein.

Example 18

PEGylation of Factor IX with mPEG-PIP, 5K

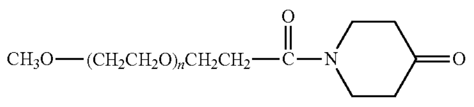

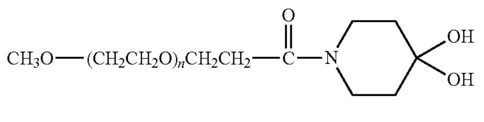

The above polymeric reagent, shown as both the ketone and corresponding ketal, is prepared as described in U.S. Patent Application Publication No. 2005/0031576.

To prepare the above polymeric reagent, to a solution of methoxy-polyethylene glycol-succinimidyl propionate having a weight-average molecular weight of 5,000 Daltons (1.0 g, 0.002 moles) in methylene chloride (20 ml), triethyl amine (0.084 ml, 0.006 moles) and 4-piperidone monohydrate hydrochloride (0.077 g, 0.005 moles) are added. The reaction mixture is stirred at room temperature under a nitrogen atmosphere overnight and then purified prior to conjugation. Alternatively, the polymer reagent may be purchased from Nektar Therapeutics.

To effect conjugation, to a solution of Factor IX in aqueous buffer is added a 20-fold molar excess of mPEG-PIP, 5K. The resulting solution is placed on a Roto Mix™ orbital shaker (Thermolyne Corp., Dubuque, Iowa) set at slow speed to facilitate reaction at room temperature. After 15 minutes, aqueous $NaCNBH_3$ is added in an amount equal to a 50 fold-molar excess relative to Factor IX. Aliquots are withdrawn at timed intervals from the reaction mixture and are analyzed by SDS-PAGE (using gels available from Bio-Rad Laboratories, Hercules, Calif.).

SDS-PAGE analysis indicates the presence of PEG derivatives of Factor IX having 1, 2, and 3 PEG moieties attached.

Example 19

Conjugation of Cysteine-Inserted Factor IX with mPEG-MAL, 20K

Factor IX is inserted with one or more cysteine residues according to the process described in WO 90/12874.

Prior to the conjugation, a buffer exchange for Factor IX is performed to replace histidine with HEPES.

mPEG-MAL, 20K, stored at −20° C. under argon, is warmed to ambient temperature. The warmed mPEG-MAL reagent (4.4 mg) is dissolved in 0.044 ml of HEPES buffer [50 mM HEPES (or other suitable buffer) pH 7.0] to make a 10% mPEG-MAL solution. The mPEG-MAL solution is quickly added to 4 ml of Factor IX solution [0.4324 mg/ml in 50 mM HEPES (or other suitable formulation) pH 7.0] and is mixed well. After 30 minutes of reaction at room temperature, the reaction vial is transferred to the cold room (4° C.), and another 0.044 ml of mPEG-MAL solution is added to the reaction mixture, followed by the addition of three more aliquots of 0.044 ml of mPEG-MAL solution over the course of two hours. The pH is determined (pH 7.0±0.2). The molar ratio of mPEG-MAL to protein is 50:1. The final mPEG-MAL concentration is 5.213 mg/ml, and the final Factor IX concentration is 0.410 mg/ml. The reaction is allowed to proceed overnight at 4° C. on Rotomix (slow speed, Thermolyne).

The conjugate mixture is purified using gel filtration chromatography. A size exclusion chromatography method is developed for analyzing the reaction mixtures, and the final products. SDS-PAGE analysis is also used for the characterization of the samples.

Example 20

In-Vitro Activity of Exemplary Factor IX-PEG Conjugates

The biological activity of each of the Factor IX-PEG conjugates described in the Examples 1, 2, 3, 9, 14 and 15 are determined. All of the Factor IX-PEG conjugates tested are determined to have some degree of Factor IX activity.

What is claimed is:

1. A composition comprising a plurality of polyethylene glycol (PEG)-Factor IX moiety conjugates, the conjugates comprising a branched polyethylene glycol covalently attached via a spacer moiety comprised of one or more atoms to a Factor IX moiety that is either Factor IX or Factor IXa, where at least about 85% of the polyethylene glycol-Factor IX moiety conjugates in the composition are monoPEGylated.

2. The composition of claim 1, wherein the branched polyethylene glycol comprises two polyethylene glycol chains attached to a polyol core.

3. The composition of claim 2, wherein the polyol core is a glycerol core.

4. The composition of claim 3, wherein the branched polyethylene glycol has a weight average molecular weight of about 40,000 daltons.

5. The composition of claim 4, wherein the branched polyethylene glycol comprises two polyethylene glycol chains each having a weight average molecular weight of about 20,000 Daltons.

6. The composition of claim 1, wherein the spacer intervening between the Factor IX moiety and the polyethylene glycol chains comprises a carbamate group.

7. The composition of claim 1, where at least about 95% of the polyethylene glycol-Factor IX moiety conjugates in the composition are monoPEGylated.

8. The composition of claim 1, wherein at least about 99% of the conjugates in the composition have from one to two of the branched polyethylene glycols covalently attached to the Factor IX moiety.

9. The composition of claim 1, wherein the branched polyethylene glycol is covalently attached to the Factor IX moiety via an amide linkage.

10. The composition of claim 1, wherein the Factor IX moiety is Factor IX.

11. The composition of claim 1, wherein the Factor IX moiety is Factor IXa.

12. The composition of claim 1, wherein the Factor IX moiety is recombinantly derived.

13. The composition of claim 1, wherein the Factor IX moiety is blood-derived.

14. The composition of claim 3, wherein the spacer intervening between the Factor IX moiety and the glycerol core of the branched polyethylene glycol comprises the structure:

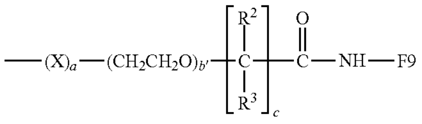

wherein (a) is either zero or one;

X, when present, is a spacer moiety comprised of one or more atoms;

(b') is zero or an integer having a value of one through ten;

(c) is an integer having a value of one through ten;

$R^2$, in each occurrence, is independently H or an organic radical;

$R^3$, in each occurrence, is independently H or an organic radical; and

F9 is a Factor IX moiety.

* * * * *

SEQUENCE LISTING

```
<160> NUMBER OF SEQ ID NOS: 1

<210> SEQ ID NO 1
<211> LENGTH: 461
<212> TYPE: PRT
<213> ORGANISM: Homo sapiens

<400> SEQUENCE: 1

Met Gln Arg Val Asn Met Ile Met Ala Glu Ser Pro Gly Leu Ile Thr
  1               5                  10                  15

Ile Cys Leu Leu Gly Tyr Leu Leu Ser Ala Glu Cys Thr Val Phe Leu
             20                  25                  30

Asp His Glu Asn Ala Asn Lys Ile Leu Asn Arg Pro Lys Arg Tyr Asn
         35                  40                  45

Ser Gly Lys Leu Glu Glu Phe Val Gln Gly Asn Leu Glu Arg Glu Cys
     50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160
```

-continued

```
Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460
```